US005667782A

United States Patent [19]

Roy

[11] Patent Number: 5,667,782

[45] Date of Patent: Sep. 16, 1997

[54] MULTIPLE PARTICULATE ANTIGEN DELIVERY SYSTEM

[75] Inventor: Polly Roy, Oxford, England

[73] Assignee: Oxford University, Oxford, England

[21] Appl. No.: 497,134

[22] Filed: Jun. 30, 1995

Related U.S. Application Data

[63] Continuation of Ser. No. 92,416, Jul. 16, 1993, abandoned, which is a continuation-in-part of Ser. No. 971,158, Nov. 4, 1992, abandoned.

[30] Foreign Application Priority Data

Jul. 16, 1992 [GB] United Kingdom .................... 9215101

[51] Int. Cl.$^6$ ......................... A61K 39/15; A61K 39/295; C12P 21/02; C12P 15/62

[52] U.S. Cl. ..................................... 424/192.1; 424/188.1; 424/189.1; 424/190.1; 424/215.1; 424/187.1; 935/47; 935/65; 536/23.4; 435/69.3; 435/235.1

[58] Field of Search ................................ 435/235.1, 69.3, 435/69.1, 172.3; 424/199.1, 192.1, 215.1, 225.1, 208.1, 186.1, 188.1, 189.1, 190.1; 935/65, 47; 536/23.4

[56] References Cited

U.S. PATENT DOCUMENTS 4,722,840 2/1988 Valenzuela ............................ 425/192.1

OTHER PUBLICATIONS

Kitson, J.D.A. et al. 1991. J. Virology, vol. 65, No. 6, pp. 3068–3075.

Lemon, S.M. et al. 1992. Virology vol. 188 pp. 285–295.

Norley, S. et al. Immunobiol. 184: 193–207 (1992).

Bowie, J et al. Science 247: 1306–1310 (1990).

Kumar, V. et al. Proc. Natl. Acad Sci 87: 1337–1341 (1990).

Roy, P. Trends. Microbiol. Jan. 8: 299–305, (1993).

French, T.J. et al. J. Virol. 64(12):5695–5700 (1990).

Eaton, B et al. Virology 180: 687–696 (1991).

*Primary Examiner*—Mary E. Mosher

*Attorney, Agent, or Firm*—Nixon & Vanderhye

[57] ABSTRACT

Antigens in particulate form are provided wherein chimeric antigens having foreign epitopes are presented on or within virus-like particles (VLPs) or virus core-like particles (CLPs). The VLPs and CLPs are immunogenic and are useful in producing vaccine formulations.

18 Claims, 15 Drawing Sheets

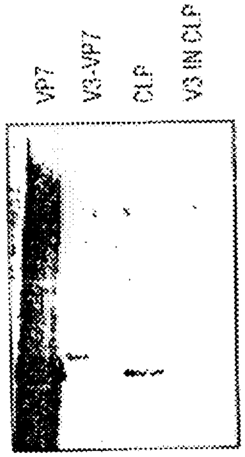

Chimeric V3-VP7 incorporated in absence of authentic VP7. A Western blot using anti BTV-10 antisera showing expression of VP7, V3-VP7 and CLP, chimeric CLP

FIG. 6A

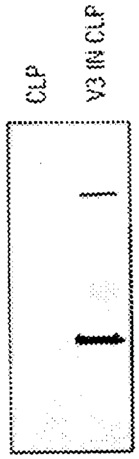

Chimeric CLPs recognised by HIV antisera. CLP, V3-CLP with anti HIV antisera. No reaction with CLP. Positive reaction with chimeric CLP.

FIG. 6B

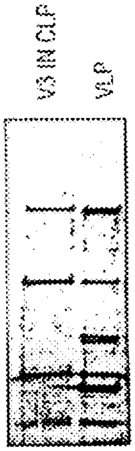

V3 loop (30 amino acid residues) incorporated in VLPs. Note mobility of chimeric V3-VP7 which is slower than authentic VP7.

FIG. 6C

FIG. 10 pAcB1-7:

```
                      ==========================
                      (M)  S   Q   A   D   Q   S   F
....GATCCTCTAGAAA ATG AGC CAA GCC GAT CAA TCC TTT

======= BLV B1 ===============================     ===
 Y   V   N   H   Q   I   L   F   L   H   L   K  (G)  D
TAT GTC AAT CAT CAA ATT TTA TTC CTG CAT CTC AAG GGG GAC

=== BTV-VP7 ====
T   ................
ACT ................
```

pAcVP3.B2-7: ===========================

FIG. 13

*Bst*XI (105 bp) site

```
         29          p8          30
 A   N   V   G   D   L   V   M
GCC AAT GTG GGG GAC CTT GTG ATG
CGG TTA CAC CCC CTG GAA CAC TAC
          p9
```

*Bst*XI (437 bp) site

```
         140         p6          141
 P   G   R   D   L   G   R   W
CCA GGG AGG GAC CTC GGG AGG TGG
GGT CCC TCC CTG GAG CCC TCC ACC
          p7
```

MULTIPLE PARTICULATE ANTIGEN DELIVERY SYSTEM

This is a Rule 62 continuation of application Ser. No. 08/092,416, filed 16 Jul. 1993, now abandoned, which is a CIP of application Ser. No. 07/971,158, filed 4 Nov. 1992, now abandoned.

This invention relates to antigens in particulate form, especially antigens in the form of virus-like particles or virus core-like particles. The invention particularly relates to chimeric antigens wherein foreign epitopes are presented on or within virus-like particles or virus core-like particles.

BACKGROUND OF THE INVENTION

Viruses generally are composed of a plurality of different proteins assembled together in a regular arrangement together with DNA or RNA. For viruses that lack a lipid envelope, the proteins are often arranged in a layered or concentric manner with certain proteins cooperating to form the outer coat or capsid and others forming the so-called core or inner capsid.

In many virus species, virus proteins are capable of assembling in the absence of nucleic acid to form so-called virus-like particles or VLPs. Similarly, the proteins which normally cooperate together with nucleic acid to form the virus core can assemble in the absence of nucleic acid to form so-called core-like particles (CLPs). As used herein, the terms "virus-like particles" and "core-like particles" will be used in the above sense to designate assemblages of virus proteins (or modified or chimeric virus proteins) in the absence of virus genomic nucleic acid.

The provision of immunogenic epitopes in entities which are in particulate form is highly desirable as such forms can be especially useful in for example the development of vaccines for oral or other mucosal routes of administration. However, relatively few useful immunogenic epitopes can readily be produced in particulate form wherein the epitopes remain immunogenic. The development of particulate vector systems for the presentation of immunogenic epitopes provides a powerful approach for the delivery of antigens. Various types of particles have been used to present foreign epitopes, including particles formed from the hepatitis B virus (HBV) surface or core antigens, polioviruses and yeast Ty-particles (1–5).

VLPs and CLPs are examples of particulate antigens that possess immnnogenic epitopes. These may often be located at or adjacent to the particle surface, although epitopes may also be located internally. Further, VLPs and CLPs are sufficiently stable and resistant to degradation to enable them to have potential use as vaccines when administered by the oral, respiratory or other mucosal routes, the latter property no doubt being associated with the fact that many viruses in native form are infectious orally. Examples of such viruses are members of the family Reoviridae.

However, attempts to modify native VLPs and CLPs in order to incorporate foreign epitopes have been fraught with difficulties as a result of several factors. First of all, it is often the case that incorporation of foreign proteins of protein fragments into VLPs or CLPs inhibits particle formation. Furthermore, even if particle formation is possible, it is uncertain whether the desired foreign epitope will be immunogenic. For example, it may be located in a site where the foreign epitope is incapable of assuming its natural conformation.

It has recently been reported that when the two major inner capsid proteins (VP3 and VP7) of bluetongue virus (BTV, Orbivirus genus, Reoviridae) are synthesized in insect cells by a dual recombinant baculovirus, viral core-like particles (CLPs) are formed (6). These particles can be isolated by one-step sucrose gradient centrifugation or by salt precipitation.

It has also been found that expression of the two major outer capsid proteins (VP2 and VP5) together with VP3 and VP7 using suitable recombinant baculoviruses results in the synthesis of VLPs. Further, expression of different combinations of minor internal proteins VP1, VP4 and VP6, both with the components of CLPs (VP3 and VP7) or VLPs (VP2, VP5, VP3, VP7), results in the inclusion of VP1, VP4 and/or VP6 into CLPs or VLPs respectively.

Further, the synthesis of CLPs can be obtained by co-expression of VP3 and VP7 species representing different serotypes of BTV or other orbiviruses such as epizootic haemorrhagic disease virus (EHDV) VP3 and BTV VP7. Further the synthesis of VLPs can be obtained with genes representing different BTV serotypes.

DESCRIPTION OF THE INVENTION

The present invention provides VLPs and CLPs which are immunogenic and especially such VLPs and CLPs which are useful in vaccine formulation. More particularly, the present invention provides genetically engineered, multi-component, virus-like particles (VLPs) and virus core-like particles (CLPs) as vaccine delivery systems for multiple immunogens representing viruses, bacteria and bacterial toxins that are responsible for human diseases (e.g. Hepatitis B, HIV, Respiratory Syncytial Virus, *Clostridium difficile*, Bovine Leukemia Virus, *Helicobacter pylori*, etc.).

According to one aspect of the present invention, there is provided an antigen in particulate form comprising a plurality of proteins capable of assembly in cooperation with one another into virus-like particles (VLPs) or virus core-like particles (CLPs), wherein the particles include first and second different proteins each of which comprises amino acid sequences derived respectively from first and second native proteins of a selected virus species and wherein at least one of the first and second proteins is chimeric and comprises an amino acid sequence derived from a foreign protein other than said first or second native protein.

According to another aspect, the invention provides a method of producing chimeric VLPs or CLPs comprising at least one non-native protein, in which the VLPs or CLPs are assembled from a plurality of different proteins including native virus proteins and the non-native protein. The non-native protein comprises an amino acid sequence derived from a foreign protein and an amino acid sequence derived from a native virus protein.

According to a further aspect, the invention provides a vaccine composition comprising an effective amount of an antigen of the invention, in association with a therapeutically acceptable carrier or diluent.

The invention also provides a method of inducing a protective immunogenic response in a host in need of treatment, wherein an immunologically effective amount of an antigen according to the invention is administered to the host. The antigen according to one aspect may be administered to a mucosal surface of said host. Suitably, the antigen is administered orally.

The present invention is based upon the surprising discovery that the above technology can be adapted to allow the formation of CLPs and VLPs which can be used to present foreign epitopes. This is based on the finding by the present inventor that the VP7 protein is located on the outer surface of the CLPs with VP3 forming an inner icosahedral subcore. Introduction of a 14 amino acid sequence representing an immunogenic region of rabies G protein to the amino terminus of VP3 results in expression of chimeric protein and the formation of CLPs when co-expressed with VP7.

Further research has now demonstrated the potential of VLPs and. CLPs as a means for constructing useful antigenic and immunogenic particles. Thus, chimeric BTV VP7 protein containing at least 48 foreign amino acids can be incorporated into CLPs and VLPs. More specifically, it has been determined that when the rabies 14 amino acid residues or amino acid residues 1–48 of the hepatitis B virus $preS_2$ region are incorporated into the amino terminus of VP7, not only are the chimeric proteins expressed in infected cells but also they can be incorporated into CLPs on co-expression with VP3.

Likewise, it has been determined that when 30 amino acids representing the V3 loop of the envelope protein of Human Immunodeficiency Virus Type 1 (HIV-1) are incorporated into the amino terminus of BTV VP7, chimeric VP7 is synthesized and incorporated into CLPs on co-expression with BTV VP3.

*Clostridium difficle* is the causative agent of colitis in humans. Toxin A plys an important role in the pathogenisis of this disease. The decapeptide TIDGKKYYFN (SEQ ID NO:37) is repeated several times in Toxin A. An oligonucleotide duplex coding for *Clostridium difficle* decapeptide Toxin A was cloned on the amino terminus of the VP7 gene using a dual vector coding for VP3 and VP7 (VP3 gene is expressed under the control of the polyhedrin promoter while VP7 gene with SmaI and SpeI (compatible with XbaI) cloning sites is placed under the control of polyhedrin promoter. *S. frugiperda* cells infected with recombinant baculovirus expressed VP3 and chimeric decapeptide VP7 CLPs.

Bovine Leukemia Virus (BLV) epitopes placed upstream of the amino terminus of BTV VP7 end cosynthesised with BTV VP3 using recombinant baculovirus did not produce CLPs. However, chimeric CLPs containing the fusion protein were produced when both unmodified BTV VP7 and the fusion protein were cosynthesised with BTV VP3.

Genes coding for the *Helicobacter pylori* urease subunits A and B were produced by PCR and cloned in the pAcUW3 vector. Recombinant baculoviruses were produced using this plasmid. *S. frugiperda* cells infected with the recombinant baculovirus produced both urease subunits A and B.

Antigens according to the invention which are in the form of CLPs generally comprise two essential proteins and one or more further optional proteins, wherein the essential proteins are virus major inner capaid proteins and the optional proteins are selected from minor inner capaid proteins. Preferably, the CLPs comprise zero, one, two or three further optional virus minor inner capaid proteins.

Antigens according to the invention which are in the form of VLPs generally comprise three essential proteins and one or more further optional proteins, wherein two of the essential proteins are virus major inner capsid proteins, one of said essential proteins is a virus major outer capsid protein, and the optional proteins are selected from minor inner capsid proteins and major outer capaid proteins. Preferably the VLPs comprise zero, or one further optional virus major outer capaid proteins and/or zero, one, two or three further optional virus minor inner capsid proteins.

Antigens in particulate form according to the invention can comprise a plurality of proteins capable of assembly in cooperation with one another into virus core-like particles (CLPs). The antigens include first and second different major structural proteins each of which comprises amino acid sequences derived respectively from first and second native proteins of a selected virus species or related virus species in the presence or absence of any one or combination of three minor proteins each of which comprises amino acid sequences derived from the three minor proteins of a selected virus species or related virus species. At least one of any of the aforementioned five proteins is chimeric and comprises an amino acid sequence derived from a foreign protein other than said native proteins.

Similarly, antigens in particulate form according to the invention can comprise a plurality of proteins capable of assembly in cooperation with one another into virus-like particles (VLPs). The antigens are characterized by including first, second, third and optionally fourth different major structural proteins each of which comprises amino acid sequences derived respectively from first, second, third and fourth native proteins of a selected virus species or related virus species in the presence or absence of any one or combination of three minor proteins each of which comprises amino acid sequences derived from the three minor proteins of the selected virus species or a related virus species. At least one of any of the aforementioned eight proteins is chimetic and comprises an amino acid sequence derived from a foreign protein other than the native proteins.

Thus, in the case of Reoviridae virus species, for example orbiviruses such as BTV, the antigens in particulate form consisting of a CLP can comprise two essential proteins and one or more further optional proteins, wherein the essential proteins are virus major inner capsid proteins VP3 and VP7 and the optional proteins are selected from the minor inner capaid proteins VP1, VP4 and VP6.

These combinations of proteins may be depicted as follows:

VP3+VP7
VP3+VP7+VP1
VP3+VP7+VP4
VP3+VP7+VP6
VP3+VP7+VP1+VP4
VP3+VP7+VP4+VP6
VP3+VP7+VP1+VP6
VP3+VP7+VP1+VP4+VP6

Similarly, VLPs can comprise three essential proteins and one or more further optional proteins, wherein two of the essential proteins are virus major inner capsid proteins VP3 and VP7, one of the essential proteins is a virus major outer capsid protein selected from VP2 and VP5 and the optional proteins are selected from minor inner capsid proteins VP1, VP4 and VP6 and major outer capsid proteins VP2 and VP5.

These combinations of proteins may be depicted as follows:

VP2+VP3+VP7
VP2+VP3+VP7+VP1
VP2+VP3+VP7+VP4
VP2+VP3+VP7+VP6
VP2+VP3+VP7+VP1+VP4
VP2+VP3+VP7+VP1+VP6
VP2+VP3+VP7+VP4+VP6
VP2+VP3+VP7+VP6+VP4+VP6

VP5+VP3+VP7
VP5+VP3+VP7+VP1
VP5+VP3+VP7+VP4

VP5+VP3+VP7+VP6
VP5+VP3+VP7+VP1+VP4
VP5+VP3+VP7+VP1+VP6
VP5+VP3+VP7+VP4+VP6
VP5+VP3+VP7+VP6+VP4+VP6

VP2+VP5+VP3+VP7
VP2+VP5+VP3+VP7+VP1
VP2+VP5+VP3+VP7+VP4
VP2+VP5+VP3+VP7+VP6
VP2+VP5+VP3+VP7+VP1+VP4
VP2+VP5+VP3+VP7+VP4+VP6
VP2+VP5+VP3+VP7+VP1+VP6
VP2+VP5+VP3+VP7+VP6+VP4+VP6

The antigens of the invention may be produced with at least one of the proteins in native form and the same protein or proteins additionally being in chimeric form, i.e. incorporating amino acid sequences of a foreign protein. Chimeric antigens in particulate form may be produced according to the invention wherein the amino acid sequence derived from the foreign protein includes an epitope which is recognized by an antibody to the foreign protein. For example, the foreign protein is a protein of a disease-producing organism and the antigen in particulate form is capable of raising protective (e.g. neutralizing) antibodies or cellular immune response in an organism susceptible to the disease. The antigens of the invention find special utility in the formulation of vaccines.

Chimeric VLPs or CLPs may include one or more of the incorporated major structural proteins in chimeric form. In this form, the CLPs may include (i) a first virus protein in native form, (ii) a second virus protein in native form, and (iii) one of the first and second virus proteins in chimeric form comprising an amino acid sequences derived from native virus protein and an amino acid sequence derived from a foreign protein.

Similarly, the VLPs may include (i) a first virus protein in native form, (ii) a second virus protein in native form, (iii) a third virus protein in native form and (iv) one of the first and second virus proteins in chimeric form comprising an amino acid sequences derived from native virus protein and an amino acid sequence derived from a foreign protein.

Chimeric VLPs or CLPs comprising at least one non-native protein are produced according to the invention by assembling the VLPs or CLPs from a plurality of different proteins including native virus proteins and the non-native protein. The non-native protein comprises an amino acid sequence derived from a foreign protein and an amino acid sequence derived from a native virus protein. The amino acid sequence derived from a foreign protein may be located at the N-terminal end of the chimeric protein, although other arrangements are also envisaged according to the invention, for example wherein the amino acid sequence derived from a foreign protein is inserted within the sequence of the native protein, or is located at the C-terminal end. It has been found that locating the amino acid sequence derived from a foreign protein at the N-terminal end of the chimetic protein enables the foreign epitope to be immunogenic in the eventual VLPs or CLPs.

Conventional techniques of site-directed mutagenesis and gene splicing may be employed in order to construct DNA sequences capable of being expressed as the chimeric protein included as a component of the antigen particles of the invention. Similarly the antigen particles may be assembled from their constituent components in a variety of ways. Thus, for example, the components may be produced separately and then simply combined by mixing solutions of the constituent proteins in a suitable medium. However, it is preferred that the native and chimeric proteins are expressed together so that assembly of the antigen particles can take place without the expressed polypeptide being degraded, modified or otherwise processed to a form incompatible with their assembly to form VLPs or CLPs. Most preferably the constituent proteins are co-expressed.

Although any suitable expression system may be employed, especially satisfactory results have been obtained using an expression system which includes a baculovirus expression vector. Thus, preferably the constituent proteins are expressed in insects or insect cells.

BRIEF DESCRIPTION OF THE DRAWINGS

The invention will now be describer in more detail with reference to the accompanying drawings, in which:

FIGS. 6A–C show a Western blot analysis carried out utilizing anti-BTV and anti-V3 (HIV-1) sera against native BTV/BTV VP7, chimetic BTV VP7/HIV-1 V3, CLPs derived from native BTV VP3/BTV VP7 and chimetic CLPs derived from BTV VP3/chimeric BTV VP7/HIV-1 V3;

FIG. 10 shows construction of BLV epitopes and BTV VP7 recombinant proteins (SEQ ID NO:19–24);

FIG. 13 shows DNA and amino acid sequences of VP7 after insertion of p8/p9 and p6/p7 oligonucleotide duplexes (SEQ ID NO:25–28). Both insertion contain unique PpUMI site (underlined) in order to use it for subsequent cloning of foreign epitopes;

EXAMPLES OF PREFERRED EMBODIMENTS

Example 1

In this Example, there is described the construction of a chimetic protein containing most of the hepatitis B virus pre$S_2$ region (amino acid residues 1–48) upstream to, and co-linear with, the amino-terminus of bluetongue virus VP7 protein (pre$S_2$-VP7).

A. Plasmid Construction

A plasmid containing a chimeric pre$S_2$-VP7 gene (FIG. 1) was generated by manipulating an EcoRI-XhoI fragment derived from the ayw subtype of hepatitis B virus (HBV) (8, 9) into the amino terminus of BTV-10 VP7 DNA in a pAcYMl-based transfer vector (pAcBTV10.7) so that it was under the control of the polyhedrin promoter (10, 11). The orientation of the chimeric gene in the transfer vector was confirmed by sequence analysis (12). To generate a recombinant virus, monolayers of *S. frugiperda* cells were co-transfected with the recombinant transfer vector and AcRP23-lacZ DNA in the presence of lipofectin (13, 14). Progeny viruses with a lacZ-negative phenotype were plaque purified and a recombinant AcBTV-pre$S_2$ virus was recovered and a high titered virus stock prepared.

Figure 1:
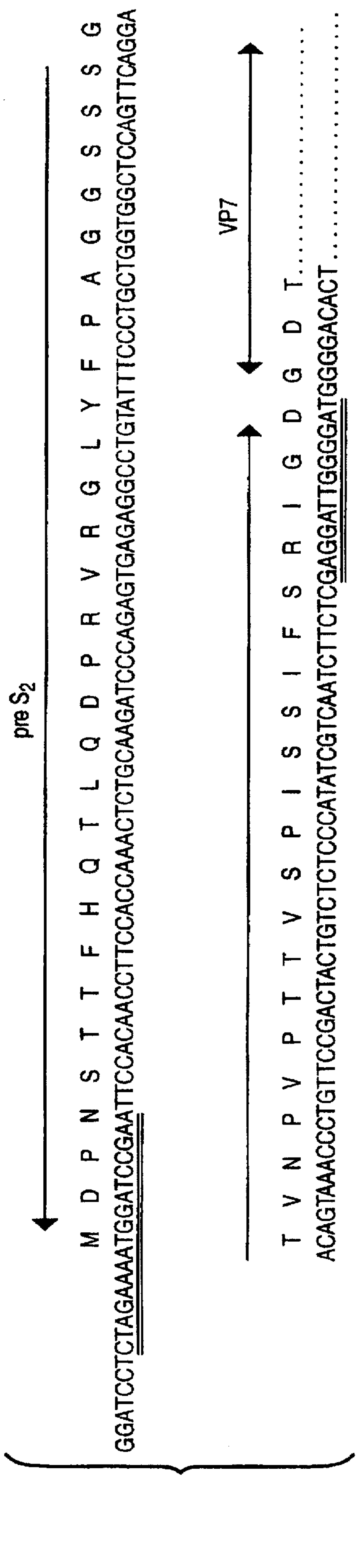
FIG. 1 shows a recombinant transfer vector containing an HBV preS$_2$ sequence upstream and colinear with BTV VP7 (SEQ ID NO:15, 16)

An oligonucleotide (5' GCGGGATCCCCTCAGACCC-GGGGACACTATCGCCGCA) (SEQ ID NO:1) was employed using the polymerase chain reaction to mutate the 5' coding region of the BTV VP7 transfer vector (15) in order to introduce upstream BamHI, SbaI and SmaI sites. Since the BTV VP7 transfer vector also contains a downstream BamHI site, the modified vector was digested with BamHI and inserted into pAcYM1 (11). The product was then digested with XbaI and SmaI and ligated to an EcoRI-XhoI fragment derived from the ayw strain of HBV (8) modified at both ends with adapters (underlined) to provide a 5' overhang complimentary to a cut XbaI sequence and a 3' blunt end. The sequence of the amino terminus of the derived chimeric gene is shown in FIG. 1.

B. Expression Of Pres$_2$-VP7

Figure 2A:
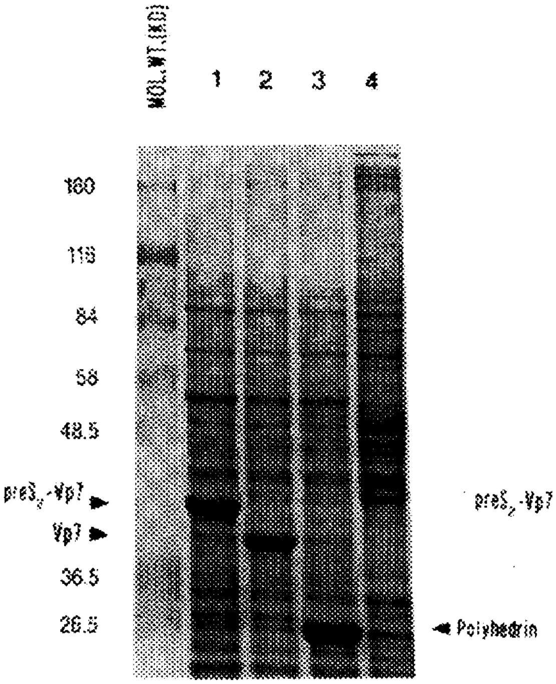
FIGS. 2A–2C show SDS PAGE analysis of proteins produced by AcBTV7-preS$_2$.
Figure 2B:
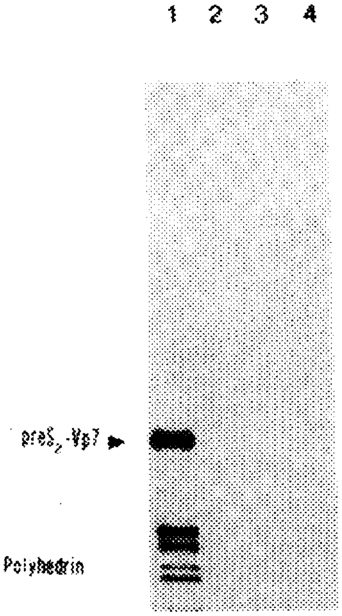
Figure 2C:
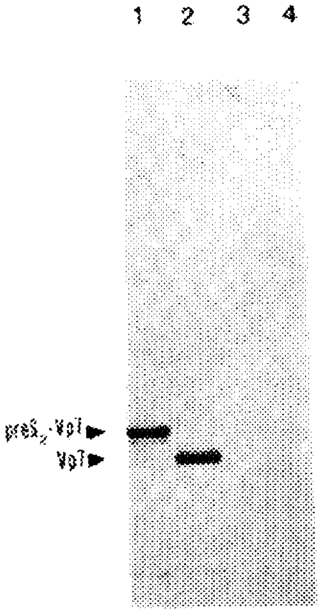

The synthesis of proteins by recombinant AcBTV7-pre$S_2$ virus was investigated by infecting monolayers of *S. frugiperda* cells with 5 plaque forming units (PFU) of AcBTV7-pre$S_2$ per cell. Cells were harvested at 48 h post-infection, lysed as described previously (6) and extracts analyzed by 10% SDS-polyacrylamide gel electrophoresis (SDS-PAGE). By comparison with wild-type AcNPV or AcBTV 10.7 that expressed only the 38 kDa VP7 protein (15), a protein of the size expected for the HBV-VP7 chimera (pre$S_2$-VP7), 43 kFDa) was identified (FIG. 2A). Confirmation that the expressed protein represented the pre$S_2$ region of HBV was provided by Western blot system analyses (FIG. 2B) using a rabbit antiserum that had been raised to an HBV pre$S_2$ peptide (amino acid residues 14–32). Both the modified and unmodified VP7 proteins reacted with antisera raised to BTV-10 virus particles (FIG. 2C).

The *S. frugiperda* cells were infected at a m.o.i. of 5 PFU per cell with AcBTVVP-pre$S_2$ (lane 1), or AcBTV10.7 (lane 2), or AcNPV (lane 3) or mock-infected (lane 4). Cell lysates were processed as described. Proteins were separated by 10% SDS-PAGE and (A) stained with Coomassie blue, or (B) were electroblotted onto an Immobilon membrane and reacted with rabbit anti-pre$S_2$, or (C) blotted and reacted with rabbit BTV-10 antiserum. Bound antibody was detected using an alkaline phosphatase conjugate. Protein molecular weight markers (KD) are shown in the left hand lane of (A). The positions of the AnNPV polyhedrin (P), pre$S_2$-VP7 and VP7 proteins are indicated.

C. Assembly Of Antigen Particles

To investigate whether the recombinant protein would assemble with BTV-VP3 protein to form CLPs (6), a suspension culture of *S. frugiperda* cells was co-infected with the AcBTV-pre$S_2$ recombinant virus and AcBTV17.3, a recombinant baculovirus that expresses only VP3 protein (16). The infected cells were harvested, lysed and analyzed by gradient centrifugation as described previously (6). Despite the high level of expression of both proteins, no morphological structures were recovered (data not shown). As a control, cells co-infected with AcBTV10.7 and AcBTV17.3 yielded CLPs (6, data not shown).

In order to determine whether there was any condition in which the chimeric VP7 could be incorporated into particles, *S. frugiperda* cells were infected with a dual recombinant baculovirus (AcBTV17.3-10.7) that expresses VP3 and VP7 (6) at a multiplicity of infection (m.o.i.) of 2 PFU per cell and the AcBTV7-pre$S_2$ virus at a m.o.i. of either 2 or 8 PFU per cell infected. Infected cells were harvested at 3 days p.i., lysed and CLPs purified by centrifugation as previously described (6).

Figure 3A:
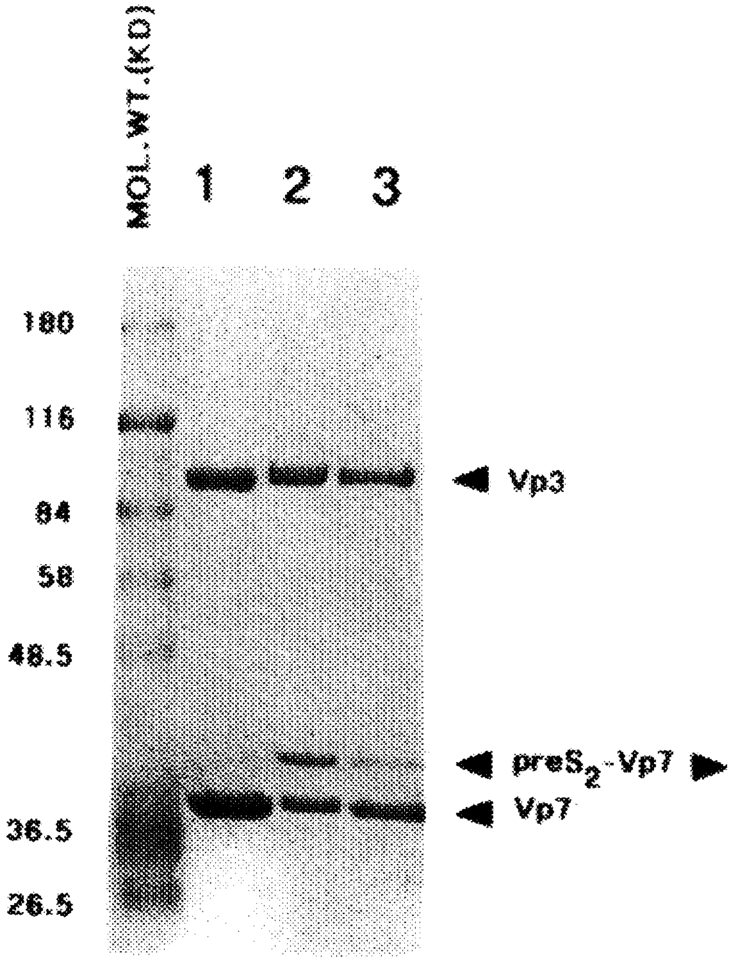
FIGS. 3A–B show SDS-PAGE and Western immunoblot analyses of CLPs composed of VP3 and VP7 (lane 1) or VP3, VP7 and preS$_2$VP7 (lanes 2 and 3)
Figure 3B:
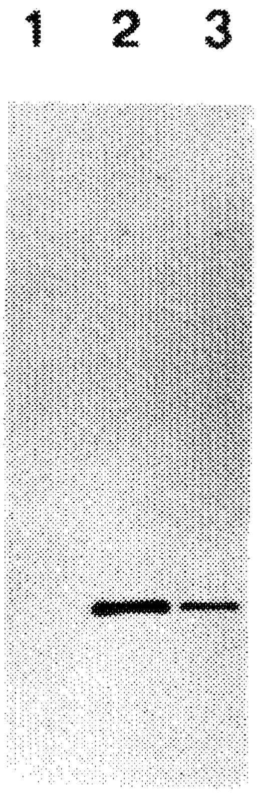

The protein profiles of the CLPs indicated that the two forms of VP7 were present in both CLP preparations (FIG. 3). However, the amount of the chimeric VP7 in the CLPs was dependent on the m.o.i. of the AcBTV7-pre$S_2$ recombinant virus used in the coinfection. At the m.o.i. of 2, the pre$S_2$-VP7 protein content relative to VP7 was significantly less than when AcBTV7-pre$S_2$ was employed at a m.o.i. of 8 (FIG. 3A). At the high multiplicity, the amount of the chimeric VP7 was estimated from the stained gel to be ca 20% the amount of authentic VP7. The presence of the chimeric protein in the particles was confirmed by 10% Western blot analysis using the HBV pre$S_2$ peptide antiserum (FIG. 3B). In FIG. 3, CLPs composed of VP3 and VP7 (lane 1), or VP3, VP7 and pre$S_2$-VP7 (lanes 2,3) were synthesized in insect cells. Purified CLPs were purified by discontinuous sucrose gradient centrifugation. Proteins were separated by 10% SDS-PAGE and stained with Coomassie blue (A), or were elctroblotted onto an Immobilon membrane and reacted with rabbit anti-pre$S_2$ serum (B). In lanes 2 and 3 the CLPs came from coinfections of AcBTV17-3, 10-7 (m.o.i. of 2) and AcBTV7-pre$S_2$ (m.o.i.=8, lane 2), or AcBTV17-3, 10-7 (m.o.i.=2), and AcBTV7-pre$S_2$(m.o.i.=2, lane 3).

Figure 4A:
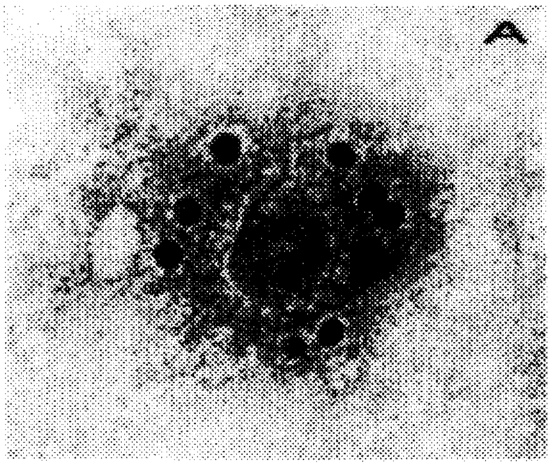
FIGS. 4A–B show immunogold-electron microscope photographs of purified CLPs.
Figure 4B:
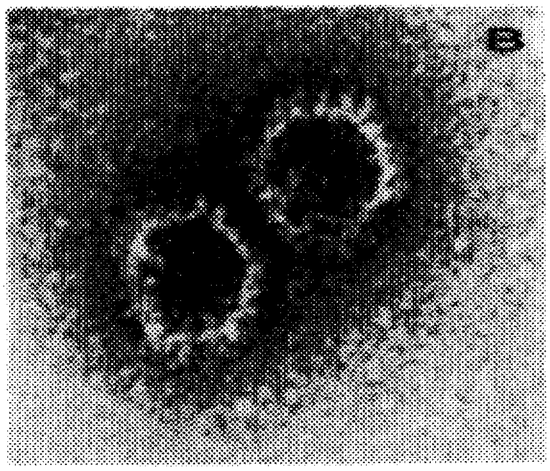

The location of pre$S_2$-VP7 protein on the particles was analyzed by immuno-electron microscopy using gold-labelled anti-HBV pre$S_2$ serum. As shown in FIG. 4A, the gold particles were located on the outer surface of the CLPs (purified CLPs obtained from coinfection of insect cells with AcVP7-pre$S_2$), indicating that the pre$S_2$ sequences were exposed on the surface of the particles. In a control experiment using CLPs derived from AcBTV17.3-10.7, no gold particles were detected (FIG. 4B—CLPs purified from cells infected only with AcBTV17.3-10.7. Bar=100 nm). When a cell lysate infected with the AcBTV17.3-10.7 dual recombinant virus was mixed with a cell lysate recovered from an AcBTVVP7-pre$S_2$ infection, CLPs were recovered and similarly analyzed by immuno-electron microscopy using gold-labelled preS antiserum. No gold particles were detected on the surface of the CLPs.

D. Immugenicity Of Chimeric CLPs

Figure 5A:
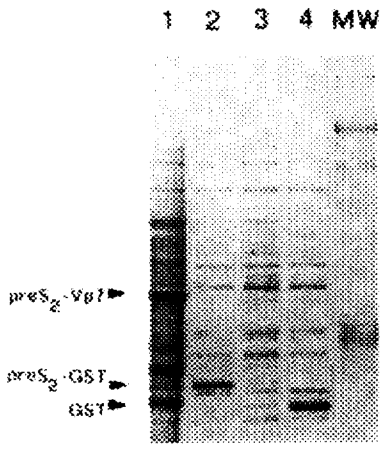
FIGS. 5A–C show SDS-PAGE and Western immunoblot analyses relating to immunogenicity of chimeric CLPs.

To demonstrate the biological activity of the chimeric CLPs, the immugenicity of these particles was assessed. Antisera against the purified chimeric CLPs was raised in mice as described previously (17) and the reactivities of the resulting antisera were examined against an expressed *E. coli* fusion protein (18) containing the pre $S_2$ region (GST-pre$S_2$ unpublished data). FIG. 5A shows the Coomassie blue stained gel of insect cells infected with recombinant baculovirus-expressing chimeric pre $S_2$-VP7 protein (lane 1), *E. coli* cells expressing GST-pre $S_2$, induced (lane 2) and non-induced (lane 3) and the GST of the control *E. coli* culture.

In Western blot analyses, both expressed proteins reacted strongly with the antibody raised against chimeric particles. The high immunogenicity was further evidenced by the reactivity of the apparently unstainable fusion protein band of the non-induced GST-pre $S_2$ with the antibody (in a 1 to 4000 titer).

Figure 5B:
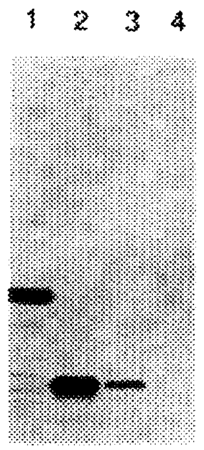
Figure 5C:
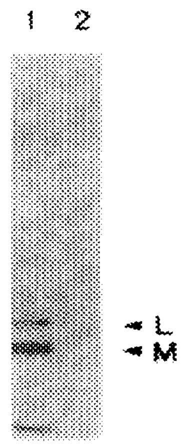

To demonstrate that the antibody can indeed recognize HBV antigen, similar Western blot analyses were performed using surface antigen positive HBV patient serum (FIG. 5C). The positive signals against large (pre $S_1$-pre $S_2$-S) and medium (pre$S_2$-S) surface antigen of HBV confirmed the high immunogenic capability of the chimetic particles.

FIG. 5 shows in particular SDS 10% PAGE (A) and Western immunoblot (B) of:

1: *Spodoptera frugiperda* cells infected with recombinant baculovirus ,expression pre $S_2$-VP7;

2: *E. coli* cells expressing pre $S_2$ epitope fused with C terminus of glutathione S-transferase (GST-pre-$S_2$) in pGEX-1 vector induced with IPTG (18);

3: the same as lane 2, without IPTG induction

4: *E. coli* cells expressing glutathione S-transferase (GST); and (C)

1: Western immunoblot with 1 HBVsAg positive patient serum; L,Large (pre$S_1$-Pre$S_2$-S) HBV surface antigen. M, medium (pre $S_2$-S) HBV surface antigen; and 2: HBVsAg negative human serum. Antibody dilution 1:4000.

Chimeric CLPs were additionally produced from BTV VP3 and a chimeric protein comprising BTV VP7 having a 30 amino acid sequence at its N-terminus derived from the HIV-1 V3 loop.

Western blot analysis was carried out utilizing anti-BTV and anti-V3 (HIV-1) sera against native BTV/BTV VP7, chimeric BTV VP7/HIV-1 V3, CLPs derived from native BTV VP3/BTV VP7 and chimeric CLPs derived from BTV VP3/chimeric BTV VP7/HIV-1 V3. The resulting blots are shown in FIG. 6 wherein Photograph A illustrates the interaction of anti-BTV sera with:

| Lane | |
|---|---|
| VP7 | native BTV VP3/BTV VP7 |
| V3-VP7 | chimeric BTV VP7/HIV-1 V3 |
| CLIP | CLPs derived from native BTV VP3/BTV VP7 |
| V3 IN CLP | chimeric CLPs derived from BTV VP3 and chimeric BTV VP7/HIV-1 V3. |

and Photograph B illustrates the interaction of anti-HIV-1 V3 sera with:

| Lane | |
|---|---|
| CLIP | CLPs derived from native BTV VP3/BTV VP7 |
| V3 IN CLP | chimeric CLPs derived from BTV VP3 and chemeric BTV VP7/HIV-1 V3. |

It can be seen that chimeric CLPs show an interaction with both anti-BTV and anti HIV-1 V3 serum whereas native BTV CLPs show no interaction to anti HIV-1 V3 sera.

VLPS were also constructed from (i) BTV VP3, (ii) a chimeric protein comprising BTV VP7 having a 30 amino acid sequence at its N-terminus derived from the HIV-1 V3 loop.

(iii) VP2, and (iv) VP5

Also referring to FIG. 6, Photograph C illustrates the interaction of anti-HIV-1 V3 sera with:

| Lane | |
|---|---|
| V3 IN VLP | chimeric VLPs derived from BTV VP2, BTV VP3, chimeric BTV VP7/HIV-1 V3 and BTV VP5. |
| VLP | VLPs derived from BTV VP2, BTV VP3 and BTV VP5. |

It can be seen that chimeric VLPs show an interaction with anti HIV-1 V3 serum whereas native BTV VLPs show an interaction to anti HIV-1 V3 sera. The mobility of chimeric VP7 is, however, lower than that of native VLPs.

Example 2

Expression of *Clostridium difficle* Toxin A decapaptide using chimeric CLP's was investigated as follows.

*Spodoptera frugiperda*(Sf) cells (ILPB-SF21) and recombinant baculoviruses were propagated as described previously (25, 26). Standard procedures were used for plasmid DNA manipulations (27). For construction of recombinant baculoviruses the transfer plasmid vectors containing foreign genes were lipofected with Bsu36.1 cut BacPAK6 DNA, and white plaques were selected and purified by two sequential plaque assays. Purification of chimeric CLPs, SDS-polyacrylamide gel electrophoresis, Western blot and electron microscopy were done as described before (28).

Figure 7:
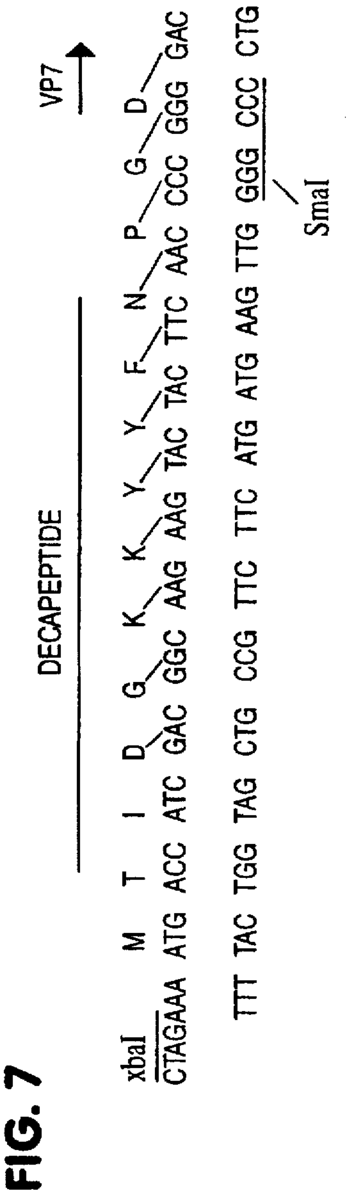
FIG. 7 shows the junction between the *Clostridium difficile* toxin A and the amino terminus of the BTV-10 VP7 (SEQ ID NO:17, 18)

Oligonucleotide duplex coding for *Clostridium difficle* Toxin A was cloned on the amino-terminus of VP7 gene (see FIG. 7). A recently developed dual vector coding for VP3 and VP7 was used for cloning the epitope in this vector. VP3 gene is expressed under the control of the polyhedrin promoter, while VP7 gene with SmaI and SpeI (compatible with XbaI) cloning sites is placed under the control of polyhedrin promoter.

Figure 8:
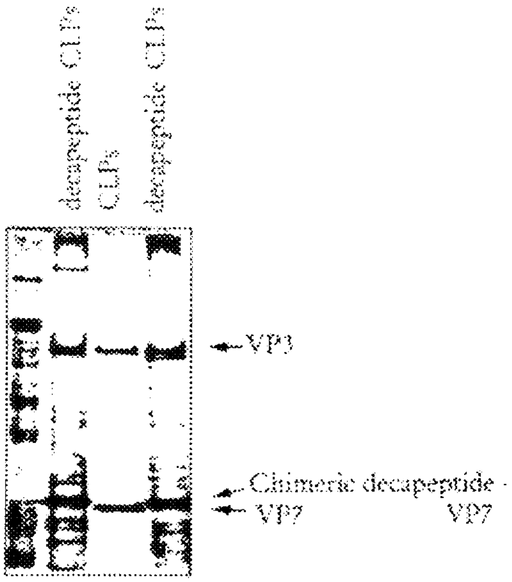
FIG. 8 shows PAGE of CLPs and chimeric CLPs carrying the *Clostridium difficile* Toxin A decapeptide.

*S. frugiperda* cells were infected with recombinant baculovirus expressing VP3 and chimeric decapeptide VP7. CLPs were produced, purified and investigated by PAGE, Western blot and electron microscopy. On the PAGE of chimetic CLPs and CLPs, it could be seen that the chimeric decapeptide VP7 is larger than unmodified VP7 (see FIG. 8).

Figure 9:
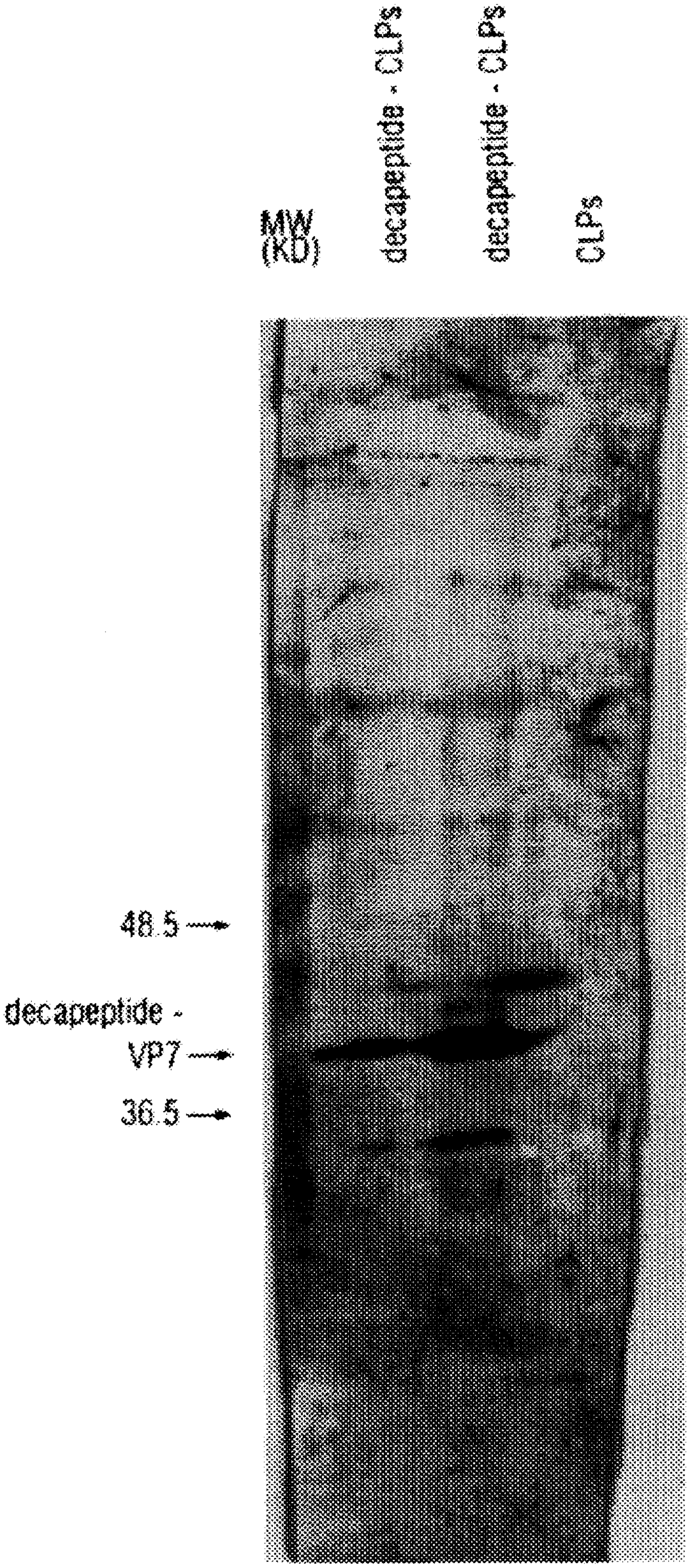
FIG. 9 shows a Western blot of CLPs and chimeric CLPs with anti-decapeptide antiserum.

Chimeric VP7, but not unmodified VP7, reacts with anti-decapeptide rabbit antibodies (see FIG. 9). On electron microscopy (uranile acetate stain), chimeric CLPs appear to be unstable, many VP7 spikes are missing, and some particles look like subcore particles.

Example 3

Expression of Bovine Leukemia Virus (BLV) epitopes using CLPs was investigated as follows.

Bovine leukemia virus (BLV) epitopes were placed upstream of the amino-terminus of VP7. Cosynthesis of the fusion protein with BTV VP3 using recombinant baculovirus did not produce core-like particles (CLPs). However, chimeric CLPs containing the fusion protein were produced when both unmodified BTV VP7 and the fusion protein were cosynthesized along with BTV VP3.

The sequences of three BLV gp51 epitopes used in this study are listed in Table 1. Transfer vectors for the recombinant baculoviruses were produced by placing annealed oligonucleotides of BLV gp51 epitope sequences (Table 2) into the amino-terminus of BTV 10 VP7 cDNA in pAcBTV10.7 (28) or pAcVC3.BTV 10.7.BTV17.3 (29) plasmids.

TABLE 1

Epitopes in BLV gp51 employed in this study

| Epitope | BLV gp51 amino acid sequence Comments |
|---|---|
| B1 | 98–117(20 residues) Syncytia inhibition |
| B2 | 169–192 (24 residues) T helper epitope and binding site to the cellular receptor |
| B3 | 142–161 (20 residues) Hinge region and contacts between gp51 molecules in the trimer |

TABLE 2

Sequence of the oligonucleotides coding for the BLV epitopes for placing into BTV10 VP7 cDNA

| Epitope | Sequence |
|---|---|
| B1 | 5'-CTAGAAAATGAGCCAAGCCGATCAAGGGTCCTTTTATGTC AATCATCAAATTTTATTCCTGCATCTCAAG-3' (SEQ ID NO: 2) 5'-CTTGAGATGCTGGAATAAAATTTGATGATTGACATAAAA GGACCCTTGATCGGCTTGGCTCATTTT-3' (SEQ ID NO: 3) |
| B2 | 5'-CTAGAAAATGAGTTTAAATCAAACGGCACGGGCCTTCCC AGACTGTGCTATATGTTGGGAACCTTCCCCTCCCTGGGC TCCCGAA-3' (SEQ ID NO: 4) 5'-TTCGGGAGCCCAGGGAGGGGAGGGTTCCCAACATATAGCAC AGTCTGGGAAGGCCCGTGCCGTTTGATTTAAACTCA TTTT-3' (SEQ ID NO: 5) |
| B3 | 5'-CTAGAAAATGAGTAAAATTCCTGATCCCCCTCAACCCGAC TTCCCTCAGCTGAACAGTGACTGGGTTCCCTCT-3' (SEQ ID NO: 6) 5'-AGAGGGAACCCAGTCACTGTTCAGCTGAGGGAAGTCGGG TTGAGGGGGATCAGGAATTTTACTCATTTT-3' (SEQ ID NO: 7) |

To generate the recombinant baculoviruses, monolayers of *S. frugiperda* cells were cotransfected with each of the three transfer vectors described above along with AcRP23-Lac Z DNA using tipofectin. Progeny viruses with Lac Z-negative phenotype were plaque purified and selected by SDS-PAGE analysis and indirect immunoperoxidase (IIP) test using anti BTV10 rabbit serum and anti BTV10 VP7 monoclonal antibody (anti-VP7 MAb). Stock recombinant viruses were checked by IIP test and Western blot analysis using the anti BTV 10 VP7 (anti-VP7) and anti BLV gp51 synthetic peptide (anti-pp) rabbit sera. IIP test.

The IIP test used was similar to that described by Sugiyama et al, (1989) Res. Vet. Sci. 46:283–285. Briefly, Sf cells infected with the recombinant baculovirus in microtitreplates were fixed with methanol, covered with blocking solution (5% Skim milk in phosphate-buffered saline), then probed with antibody followed by peroxidase-protein A (Bio Rad). Bound peroxidase-protein A was visualized using o-phenylenediamine.

Infected Sf cells and CLPs were analyzed by SDS-PAGE after SDS-mercaptoethanol treatment. Proteins were Western blotted to Immunobilon membrane (Millipore Corp.) which were then soaked overnight in blocking solution, prior to probing with anti-VP7 or anti-pp sera followed by peroxidase-protein A, and detection using ECL system (Amersham).

The orientation of the chimeric gene in the transfer vectors were confirmed by sequence analysis (FIG. 10). Construction of the recombinant baculoviruses expressing BLV B1-BTV10 VP7 chimera (AcB1-7) and BLV B3-BTV VP7 chimera and VP3 (AcVP3.B3-7) have been completed. The plaque purification of another recombinant virus, AcVP3.B2-7, is in progress. As shown in Table 3, all three recombinant virus proteins reacted with anti BTV10 rabbit serum and anti-VP7 MAb.

TABLE 3

Immunoreactivities of antibodies with the recombinant baculovirus-infected Sf cells in IIP test

| | Recombinant baculoviruses | | | |
|---|---|---|---|---|
| antibody | AcNPV | AcB1–7 | AcVP3.B2–7 | AcVP3.B3–7 |
| Anti BTV10 | – | + | + | + |
| Anti-VP7 MAb | – | + | + | + |
| Anti-pp(98–117) | – | + | NT* | – |
| Anti-pp(142–161) | – | – | NT | + |

*NT; Not tested

AcVP3.B3-7-infected Sf cells also reacted with anti-pp (amino acid residue 142–161) rabbit serum, but AcB1-7 proteins did not react with anti-pp(98–117) rabbit serum. However, since the anti-pp(98–117) serum also did not react with BLV gp51 antigen (Table 4), the expression of BLV B1 using anti BLV gp51 or anti BLV rabbit sera is being checked.

TABLE 4

Immunoreactivities of antibodies with recombinant baculovirus-infected Sf cell lysate and BLV gp51 antigen in western blot

| antibody | Recombinant baculovirus | | | BLV gp51 |
|---|---|---|---|---|
| | AcVP3-7 | AcB1-7 | Ac:VP3.B3-7 | |
| Anti-VP7 serum | + | + | + | NT |
| Anti-pp(98–117) | – | – | – | – |
| Anti-pp(142–161) | – | – | + | + |

TABLE 5

Formation of chimeric CPS.

| Recombinant baculovirus | CLP-formation |
|---|---|
| Chimeric AcB1-7 + AcBTV17.3 | No |
| Chimeric AcB1-7 + AcBTV10.7-17.3 | Yes |
| Chimeric AcVP3.B3-7 | No |
| Chimeric AcVP3.B3-7 + AcBTV10.7 | Yes |
| Chimeric AcVP3.B3-7 + AcBTV10.7-17.3 | Yes |

| | BglII | |
|---|---|---|
| Direct primers: | M E I L G I(SEQ ID NO:10) | |
| MEI | GGC<u>AGATCT</u>ACC.ATG.GAA.ATT.TTG.GGG.ATA.G(SEQ ID NO:9) | |
| (29 aa deletion) | BglII | |
| | M A Q R N E M(SEQ ID NO:12) | |
| MAQ | GGC<u>AGATCT</u>ACC.ATG.GCA.CAA.AGA.AAT.GAG.ATG.T(SEQ ID NO:11) | |
| 55 aa deletion | BglII | |

Figure 11A:
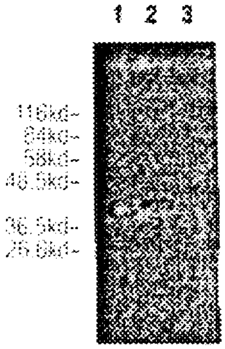
FIGS. 11A and B shows Western blot for expression of recombinant baculoviruses. Recombinant virus-infected Sf cell lysate were blotted on the membrane and reacted with (A) anti-VP7 rabbit serum and (B) anti-pp(142–161) rabbit serum. Lane 1; AcVP3.7. Lane 2; AcVP3.B3–7; AcVP3.B1–7.
Figure 11B:
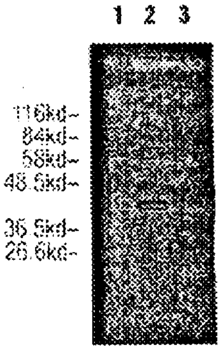

Estimation of molecular weights using western blot analysis showed that the chimeric proteins B1-VP7 and B3-VP7, and BTV VP7 were 40 kd, 42 kd and 38 kd as expected (FIG. 11A).

Formation of chimeric CLP.s

Figure 12A:
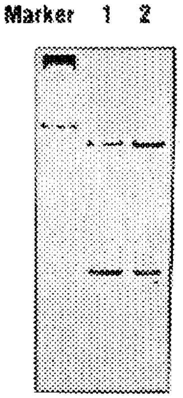
FIG. 12 shows SDS-PAGE (A) and Western blot analysis (B) of chimeric CLPs using anti-VP7 rabbit serum (a) and anti-pp (142–161) rabbit serum (b). Lane 1; Normal CLPs, Lane 2; chimeric CLPs (B3–7)
Figure 12B:
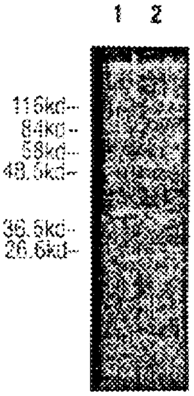
Figure 12B:
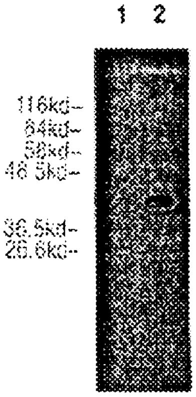

CLPs were not formed in Sf cells coinfected with AcB1-7 and AcBTV17.3 or infected with AcVP3.B3-7 even though there was high levels of synthesis of both proteins (Table 5). Chimeric CLPs formed only when cells were coinfected with these recombinant viruses and a recombinant baculovirus expressing authentic VP7. The presence of the chimeric protein (B3-7) in the CLPs from the Sf cells infected with AcVP3-7 was confirmed by western blot analysis using the anti-VP7 and anti-pp (142–161) rabbit sera (FIG. 12).

Example 4

Expression of Hepatitis B preS₂ epitopes using modifications and variations of the VP7 gene was carried out as follows.

S. frugiperda cells (ILPB-Sf21) and recombinant baculoviruses were propagated as described previously (25, 28). Standard procedures were used for plasmid DNA manipulations (27). Polymerase chain reaction (PCR) with subsequent proteinase K digestion was performed as described (30). For construction of recombinant baculoviruses the transfer plasmid vectors containing foreign genes were lipofected with Bsu36I cut Bac PAk6 DNA, white plaques were selected and purified by two sequential plaque assays (31). Purification of chimeric CLPs, SDS-polyacrylamide gel electrophoresis, Western blot and electron microscopy were done as described before (28).

Amino terminal deletions

VP7 vector used in our previous studies utilizes amino terminus of VP7 for attachment of foreign epitopes, though epitopes as large as 50 aa can be expressed on the surface of chimeric CLPs, the vector system usually needs co-infection with some unmodified VP7. Otherwise in most cases particles are not formed or are unstable.

Therefore, amino terminal deletions of VP7 were constructed in order to extent the capacity of VP7 as a vector. If amino terminal sequences of VP7 are not necessary for the formation of CLPs, then they can be substituted for other amino acid sequences (foreign epitopes) and the larger sequences (more than 50 aa) can be inserted.

Two amino terminal deletions of VP7 were constructed by the PCR technique using reverse primer: GGCGAGATCT-TA.AGA.GAC.GTT.TAATG.GG (SEQ ID NO:8)

PCR fragments obtained with these primers were treated with proteinase K, phenol and ethanol precipitated. After digestion with BglII restriction endonuclease PCR fragments were cloned into BamHIsite of pAcYM1 baculovirus expression vector (32). Recombinant viruses were obtained using BacPAK6 linearized baculovirus DNA (31). Expression of amino terminus truncated VP7 proteins was verified on the Coomassie blue stained polyacrylamide gels. As expected, truncated VP7 proteins had molecular weights 24 kD(29 as deletion) and 30 kD (55 as deletion).

For production of CLPs, S. frugiperda cells were co-infected with recombinant baculovirus expressing VP3 and recombinant baculoviruses expressing either VP7 (29 aa deletion), VP7 (55 aa deletion) or VP7 as a positive control. Cells were lysed 48 hr post-infected and CLPs were purified as described previously (28). CLPs were produced only in control experiments with the undeleted VP7, but not with its truncated variants from which we concluded that amino terminal portion of VP7 is essential for formation of CLPs, and therefore replacement with foreign sequences is not possible.

Insertions to the hydrophilic regions of VP7

The aim was to determine the regions within the VP7 molecule, that are able to carry extra sequences, since such regions could be advantageous for expression of conformational epitopes. Development of such vectors are essential as that the majority of immunogenic epitopes is conformational.

Hydrophilic regions of VP7 have been targeted as, in general, hydrophobic regions are needed for intra-inter molecular interactions.

Two BstXI sites (position 105 and 937 bp) were used to insert amino acid sequences into VP7. Both sites are situated in parts of the VP7 gene coding for hydrophilic regions of VP7. For the first site (position 105), the VP7 tertiary structure is known. Amino acid insertions into it should be situated in the loop between A and B β-sheets, therefore X-ray crystalographic studies are required. Therefore it can be expected that insertions into this site should not disturb the tertiary structure of VP7.

In order to test the possibility of using these sites for expression of foreign epitopes, oligonucleotide duplexes coding for four amino acids each were synthesized (FIG. 13).

pUC4K-BTV-10 S7 plasmid containing S7 gene cloned in the BamHI site of pUC4K vector was digested with BstXI restriction endonuclease and p6/p7 and p8/p9 oligonucleotide duplexes were ligated into it separately.

Figure 15:
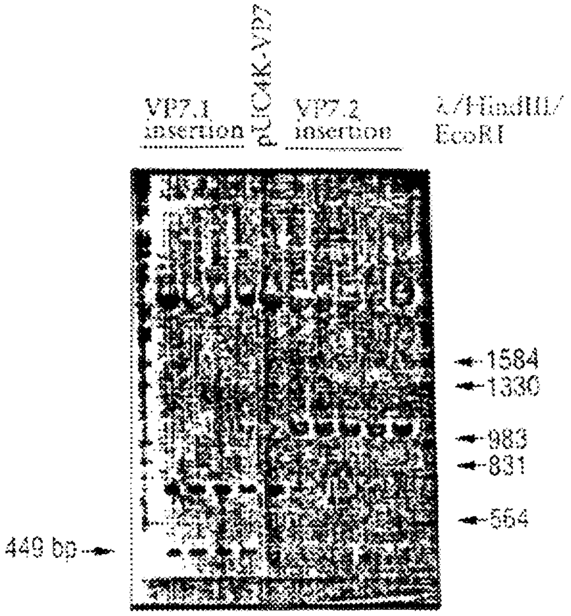
FIG. 15 shows agarose gel electrophoresis of BamHI/BstXI digests of initial pUC4K-BTVI-VP7 and the clones with insertions. Fragments smaller than 350 b.p. run out of the gel.
Figure 14:
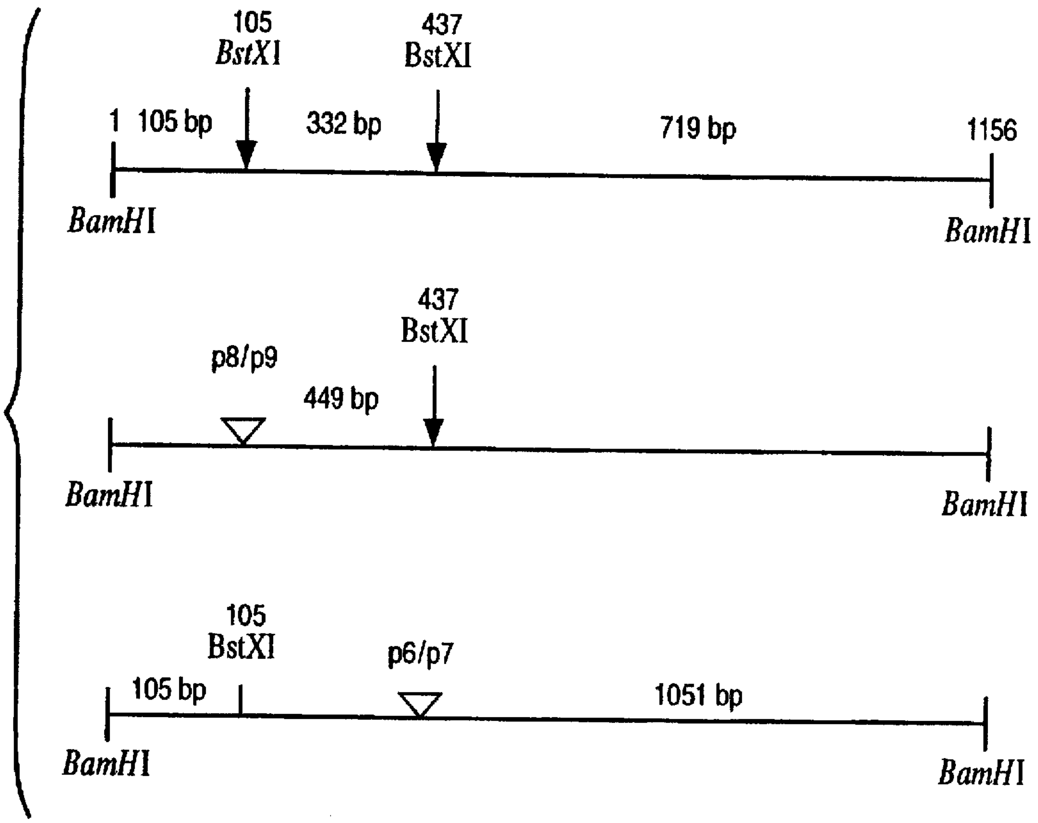
FIG. 14 shows the BsXI maps of the initial VP7 gene and the genes with insertions.

The resulting clones were checked by digestion with the BamHI and BsXI restriction endonucleases (FIGS. 14 and 15). VP7 genes with insertions were excised out from the pUc4K vector and recloned into the BamHI cut and dephosphorylated pAcYMI vector (32), and verified using BsXI digestion.

Recombinant baculoviruses expressing VP7 variants with insertions were produced as described above. *S. frugiperda* cells were coinfected with recombinant baculoviruses expressing VP3 and VP7 with insertions. CLPs were produced with unmodified VP7, but not with VP7 variants carrying 4 aa insertions. Therefore, it was concluded that sites which were used for insertions are not suitable for vector purposes.

Internal Point Mutations

Figure 16:
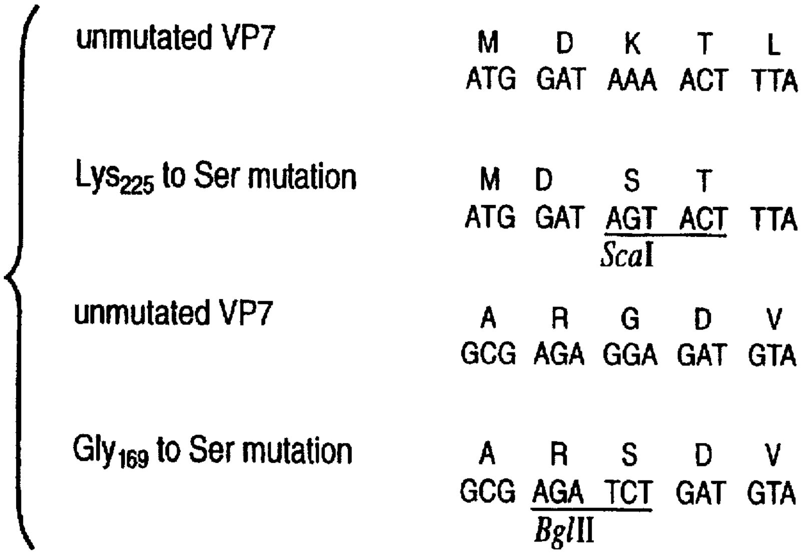
FIG. 16 shows mutations of VP7 with creation of cloning sites (SEQ ID NO:29–36)
Figure 17:
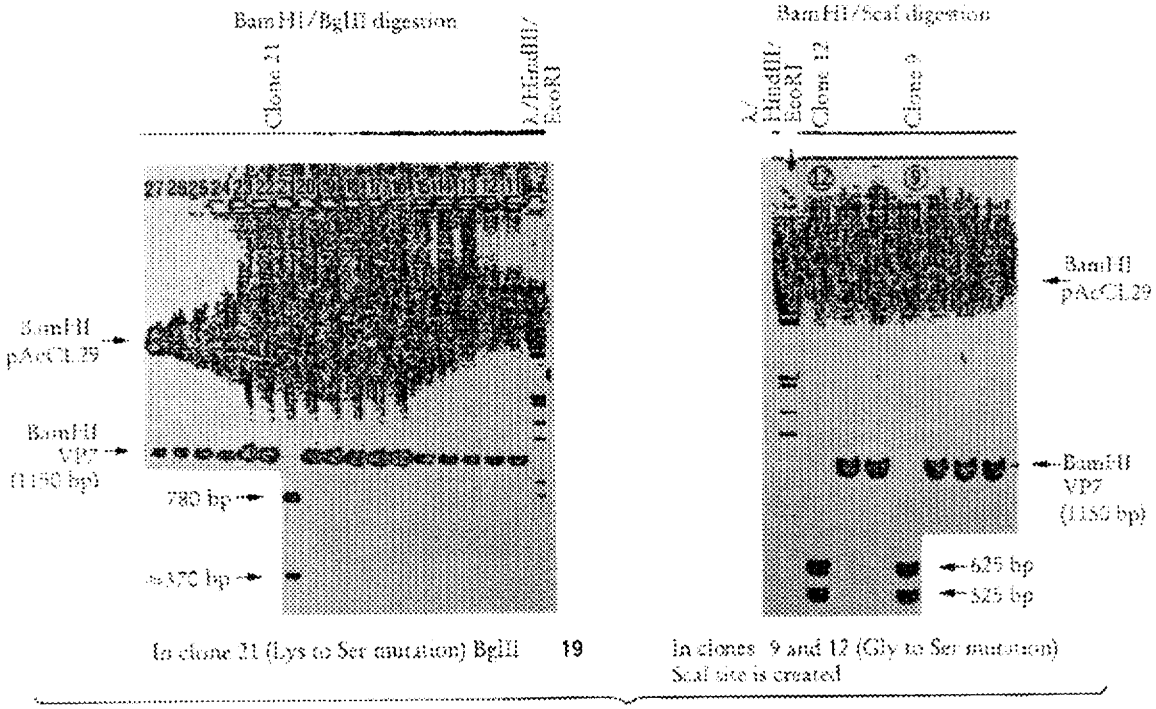
FIG. 17 shows restriction endonuclease analysis of mutated VP7 genes with created BglII and ScaI sites.

Two different point mutations of VP7 gene were prepared with the simultaneous introduction of unique cloning sites in order to use them for cloning of foreign immunogenic epitopes. BTV10 VP7 gene was cloned in BamHI site of the pAcCL29 plasmid baculovirus expression vector with single-stranded capacity (8). The mutations are shown on FIG. 16. Restriction endonuclease analysis of mutated genes is shown on FIG. 17.

One mutation is a change of Lys255 to Ser creating a ScaI site, and another is a change of Gly169 to Ser which creates the BglII cloning site. The second mutation is of particular interest, because it mutates RGD motif of VP7 which is often involved in cell receptor binding. Therefore, it is probably that RGD motif is on the surface of CLPs, and may be used for presentation of foreign epitopes.

Recombinant baculoviruses expressing mutated VP7 genes have been constructed. In experiments where *S. frugiperda* insect cells were co-infected with recombinant baculoviruses expressing VP3 and mutated VP7s (separately), it has been established that both mutations permit the formation of CLPs. However, in the case of Lys to Ser mutation, CLPs appeared to be incomplete and lacking some VP7. In case of Gly to Ser mutation, perfect CLPs were formed, which had no visible difference from CLPs produced with unmutated VP7. This site will be developed for cloning foreign immunogenic epitopes.

Example 5

Expression of *Helicobacter pylori* urease subunits A and B epitiopes as CLPs was investigated as follows. *Helicobacter pylori* is a causative agent of peptic ulcer. Production of *Helicobacter pylori* urease is of interest for the development of a vaccine against this disease (33).

Dual baculovirus expression vector pAcUW3 was used for the expression of both A and B subunits of *Helicobacter pylori* using single baculovirus (34). Polymerase chain reaction (PCR) was performed as described (30). For construction of the recombinant baculovirus, the plasmid transfer vector containing urease A and B subunits was lipofected with Bsu36.1 cut BacPAK6. DNA, white plaques were selected and purified by two sequential plaque assays (31). Polyacrylamide gel electrophoresis were done as described before (28).

Genes coding for the *Helicobacter pylori* urease subunits A and B were produced by PCR, using 2.7 kb TaqI clone (W. Thomas) as a template. PCR fragments containing structural genes coding for the urease subunits were cloned in the pAcUW3 vector, urease A subunits in the BgHI site, under the control of the polyhedrin promoter. Orientation of PCR fragments in the pAcUW3 A, B. plasmid was established using HindIII restriction endonulclease.

Figure 18:
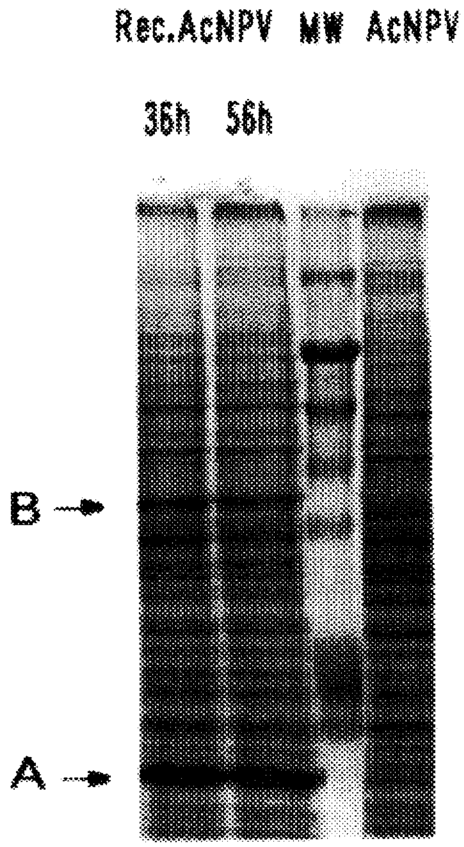
FIG. 18 shows PAGE of the lysates of *S. frugiperda* cells infected with recombinant baculovirus expressing the *Helicobacter pylori* urease A and B subunits.
Figure 19:
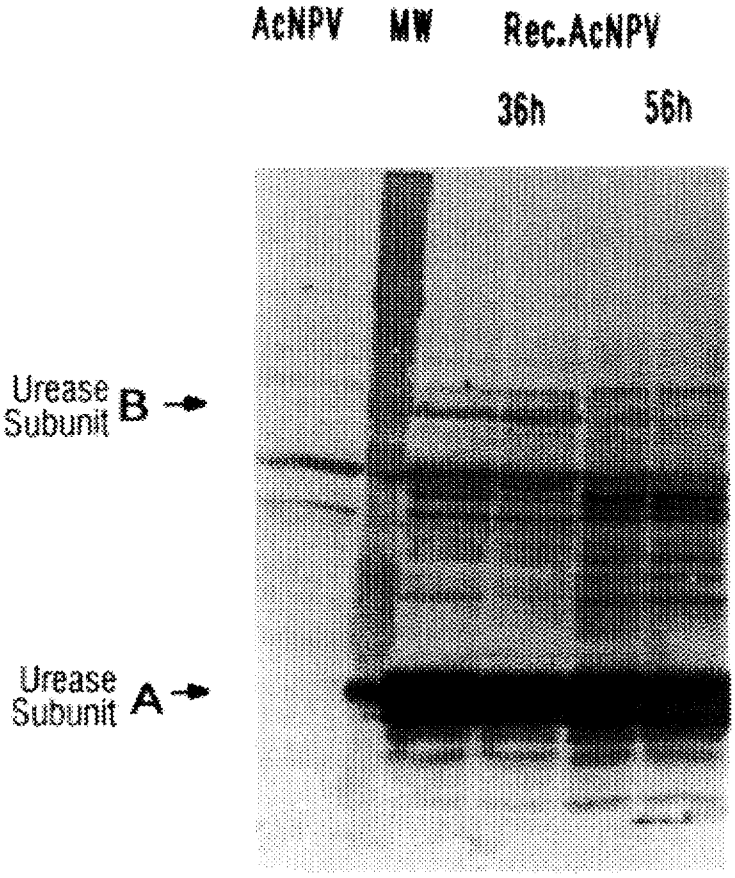
FIG. 19 shows Western blot of the lysates of *S. frugiperda* cells infected with recombinant baculovirus expressing the *Helicobacter pylori* urease A and B subunits.
Figure 20:
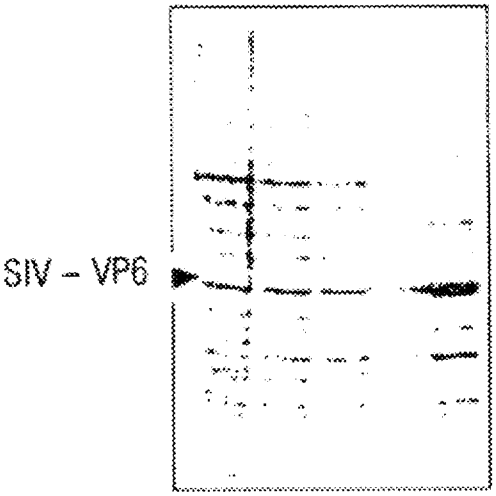
FIG. 20 shows 10% SDS-PAGE showing expression of SIV VP6 in insect cells.
Figure 21:
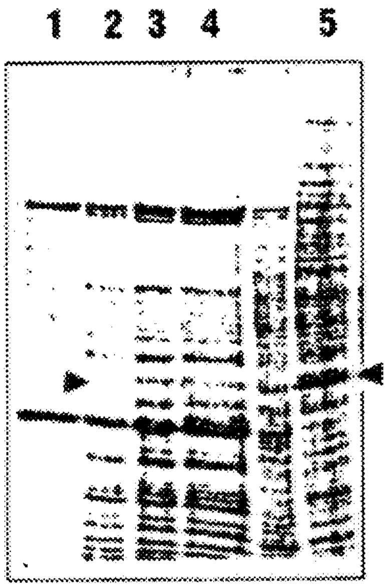
FIG. 21 shows SDS-PAGE of CLPs with SIV VP6—Lane 1 only CLPs; Lanes 2, 3 and 4 with different amounts of CLPs with SIV VP6; Lane 5 only SIV VP6.

Recombinant baculoviruses were produced using this plasmid. When *S. frugiperda* cells were infected with this recombinant baculovirus, both urease A and B subunits were produced (FIG. 18). Both A and BV subunits react with anti-urease antibodies on the Western blot (FIG. 19). Expression of the subunit A was very good, whereas the subunit B was not expressed to such a high level. Subunit B appears to be highly unstable, a ladder of urease-specific bands could be seen on the Western blot. This might be one of the reasons for its modest expression.

Example 6

It has been demonstrated previously that the three minor proteins of BTV, VP1, VP4 and VP6 can be incorporated into CLPs when expressed by baculovirus vectors. The present example describes efforts to determine whether these proteins could be developed for the delivery of foreign epitopes within the CLPs. To this end, the present example describes efforts to exploit VP6 proteins by deletion mutations and subsequently insertion of the foreign epitope. The deletion of carboxy termini of VP6 has been demonstrated to be encapsidated within CLPs.

A chimeric protein with a T-helper epitope from the gag gene of SIV (41 to 62) amino acid) on the carboxy terminus (HindIII site by removing 23 amino acids) of VP6 protein of BTV was constructed. The resulting protein was encapsidated in the core-like particles (CLPs).

The SIVgag epitope was synthesised by PCR using the standard protocol. The cloned SIVgag gene was used as the template and the following nucleotides as primers:

| | | |
|---|---|---|
| 1. | Forward primer<br>HindIII | |
| 5' | CGCGAAGCTTCGCAAGCACTGTCAG AAGG(SEQ ID NO:13) | |
| 2. | Reverse primer<br>HindIII BamHI | |
| 5' | GCGCAAGCTTGGATCCTATTGATGG TCTC C(SEQ ID NO:14) | |

A HindIII site on the forward and HindIII and BamHI sites on the reverse primers were kept.

Construction of Chimeric Plasmid

The plasmid pUC19 containing VP6 cDNA was digested with HindIII and the large fragment gel purified. The PCR synthesised HindIII digested fragment was cloned into the gel purified large fragment and the orientation and sequence was checked by sequencing.

Construction of Transfer Vector

The chimeric VP6 SIV gene was excised from pUC19 by digestion with BamHI and cloned at the BamHI site by the baculovirus transfer vector pAcYM1. The orientation was checked by sequencing.

Preparation of recombinant baculovirus expressing SIV epitope with BTV VP6

A monolayer of Sf21 cells was co-transfer vector and Bsu361 digested baculovirus bakPac6 DNA. The supernatant containing the progeny viruses was collected at 60 hr. p.i. and the recombinant viruses were plaque purified (white plaques) against wild types (blue plaques).

Encapsidation of SIV VP6 in CLPs

The cells were co-infected with a dual recombinant baculovirus expressing VP3 and VP7, and SIV VP6 recombinant baculovirus. The CLPs were purified at 48 hr p.i.

Construction of recombinant baculovirus expressing SIV VP6 chimeric protein

The construction of this recombinant is complete. The expression of the chimeric protein was analyzed by in vitro labelling with 35S methionine and SDS-PAGE (compared with the native VP6 protein). Both have the same molecular weight as 23 amino acids are deleted from the native VP6 and 23 have been added to the chimeric protein (gag epitope).

Encapsidation of SIV VP6 in CLPs

On co-infection with dual recombinant virus, SIV VP6 was encapsidated within the CLPs formed by VP3 and VP7.

Currently, large quantities of CLPs containing SIV-VP6 have been prepared and inoculated into mice. Evaluation of the immunogenicity of the chimeric SIV, mainly be T cell responses is underway. The future plan is to exploit VP6 proteins for presentation of T cell epitopes of foreign immunogens.

The vaccines of the invention in are formulated by methods known in the art, such as for example by simple mixing. The vaccines are employed in amounts readily determined by one of ordinary skill. For adults, a suitable dosage is in the range of 10 μg to 100 mg, for example 50 μg to 50 mg. Similar dosages will be applicable for children. Carrier systems for humans may include enteric release capsules protecting the antigen from the acidic environment of the stomach.

Adjuvants may also be employed. A suitable mucosal adjuvant is cholera toxin. Others which may used are non-toxic derivatives of cholera toxin. The amount of adjuvant employed depends on the type used. Typically, when cholera toxin is employed, it is used in an amount of about 5 μg to 50 μg, e.g. 10 μg to 35 μg. Suitable carriers are enteric capsules and polylactide-glycolide microspheres. Suitable diluents are 0.2N $NaHCO_3$ and/or saline.

Preferred modes of administration are orally, nasally, rectally or ocularly. Oral administration can provide delivery to other G.I. mucosa including intestinal mucosa. The vaccine may be administered to mucosal surfaces as an aerosol, suspension, capsule, and/or suppository. The method of administration will be readily apparent to a person of ordinary skill in this art.

In summary, BTV structural protein chimeras have been constructed based on VP7 containing well-studied immunogenic regions of various foreign viral antigens (e.g., rabies virus glycoprotein G, hepatitis B virus $preS_2$ region, HIV and SIV gag and env proteins). A 10 amino acid residue sequence representing an immunogenic region of rabies G protein was introduced to the amino terminus of VP7 and the chimeric protein was expressed by a recombinant baculovirus and incorporated into CLPs and VLPs on co-expression with other BTV proteins. The particles have been used to elicit immune response in mice and shown to produce sera that recognize, by Western blot analysis, authentic rabies G protein. Similarly a chimeric VP7 protein containing most of the hepatitis B virus $preS_2$ region (amino acid residues 1–48) upstream to, and co-linear with the amino-terminus of VP7 protein ($preS_2$-VP7) was expressed and incorporated into the CLPs in the presence of authentic VP7 and VP3. Both VP7 proteins were incorporated into CLPs. The ratio of $preS_2$-VP7 incorporated into CLPs was influenced by the expression level of authentic VP7. Immunoelectron microscopy of the chimeric particles indicated that the $preS_2$ epitope was exposed on the surface of the CLPs.

For HIV and SIV gag and env protein three different regions for insertion into chimeric VP7 (e.g., the VP3 loop of HIV-1 env, the amino acid residues 41–60 of SIV gag, and the amino acid residues 161–180 of SIV gag protein) have been tested. Each of these epitopes were fused with the amino-terminus of BTV VP7 protein and expressed by recombinant baculoviruses. Each recombinant virus was then used to infect insect cells together with a second recombinant virus expressing the BTV VP3 protein in order to form CLPs. Both biochemical and electron microscopic analyses indicated that the chimeric CLPs were formed that were similar to the BTV CLPs. Immunogold-negative stain electron microscopic analyses revealed that these epitopes were exposed on the surface of CLPs. Chimeric VLPs were also constructed in which the V3 loop of the HIV any protein was inserted into the N-terminus of BTV VP7 and co-expressed with recombinant baculoviruses expressing VP3 as well as (1) BTV VP2 and (2) BTV VP5.

The data obtained indicates that when a large epitope, e.g. the 48 amino acids of HBV $preS_2$ was incorporated into the amino terminus of BTV VP7, it blocked the formation of CLPs on co-expression with BTV VP3. However when co-expressed with a dual gene vector that made VP7 and VP3 the chimetic protein was incorporated.

By contrast when a small epitope, e.g. the 10 amino acid sequence representing a rabies G sequence, was incorporated into the VP7 amino terminus, CLPs were formed on co-expression with VP3 alone. Similarly, it has been found that using chimetic VP7 including an N-terminal sequence derived from the hypervariable region of the HIV V3 loop (30 amino acid residues) CLPs can be formed in the absence of authentic VP7 protein.

The VP7 of BTV exists on the surface of CLPs as trimera. Recent analyses have shown that when insufficient VP7 is made in co-infections with vectors that synthesize large quantities of VP3, incomplete CLPs are produced, CLPs that lack some of the surface arrangement of VP7. It is possible that VP7 is added sequentially to the VP3 subcore, first to positions that stabilize the structure and second to positions that complete the CLP surface structure. By this model, when a chimeric VP7 is unable to produce a CLP with VP3 alone, supplementation with unmodified VP7 protein allows incorporation of the chimetic protein.

The present invention is concerned with the expression of chimeric VP7 proteins containing 48 amino acid residues of the hepatitis B virus (HBV) pre-$S_2$ region, 30 amino acid residues of the HIV-1 V3 loop, and 10 amino acids of rabies virus G-protein. The chimetic VP7 proteins were expressed in baculovirus together with native BTV structural proteins to produce chimetic CLPs and VLPs.

In the case of the largest chimeric protein, VP7/HBV pre-$S_2$, the protein, although not included into CLPs when expressed with VP3, was included into CLPs when co-expressed with VP3 and VP7, indicating that the particles can accommodate various forms of VP7. The biological and immunological characteristics of these particles have been analyzed. The HBV epitopes were localized to the surface of the CLPs as demonstrated using immunogold electron microscopy.

The chimeric protein formed BTV corelike particles (CLPs) in *S. frugiperda* cells only when the cells were co-infected with this recombinant virus and a recombinant baculovirus that expresses unmodified VP7 and VP3 of BTV. The ratio of $preS_2$-VP7 incorporated into CLPs was influenced by the relative multiplicities of infection of the two viruses. Immuno-electron microscopy of the chimeric particles indicated that the $preS_2$ epitope was exposed on the surface of the CLPs. When insect cells were co-infected with the $preS_2$-VP7 recombinant virus and a baculovirus vector that synthesized only the VP3 protein, no CLPs were identified.

The synthesis of high levels of BTV chimeric CLPs offers a novel approach for presenting large epitopes. The immunogenity of foreign epitopes presented by such CLPs was demonstrated in mice.

In addition to the epitopes presented as part of the chimeric protein of the VLPs or CLPs of the invention, the structure of typical VLPs and CLPs can allow additional antigens to be incorporated, for example in a hollow central region. Thus multivalent vaccines can be produced utilizing the procedures described herein.

CLPs and VLPs produced according to the invention offer several particular advantages over other systems. First, large quantities can be produced, especially when use is made of the expression capabilities of baculovirus vectors (e.g. the potential for production at 20–30 mg per liter culture, the potential for production in serum-free medium, and stability to freeze-drying). Second, CLPs and VLPs can be purified using a one-step generic protocol based on the physical properties of the particle (gradient centrifugation of cell lysates). Third, they can be produced in a form which is substantially devoid of any detectable amounts of foreign e.g. insect, or baculovirus proteins and of RNAs or DNAs. Fourth, purification procedures can be used which are gentle enough to maintain the morphological structure of the particles in their native conformations. Fifth, the particles can be made in a form which do not replicate although they can efficiently attach to and be taken up by cells. Sixth, CLPs and VLPs, especially those based on BTV, can tolerate a wide range of additional protein sequences without disruption, allowing multiple epitopes to be accommodated. Lastly, and most important, VLPs can be produced which have inherent properties of inducing both B cell and T cell responses in vertebrate hosts.

In summary, CLPs and VLPs have been developed which can deliver multiple peptide components representing viral epitopes in order to elicit protective immunity. The CLPs and VLPs, especially those of BTV, are large multiprotein structures.

They can incorporate alternative protein forms of the structural proteins (e.g., chimeric VP7), including alternative forms of these proteins (e.g. VP7a and VP7b). In addition, there is a possibility to use more than one of the protein types to deliver antigens (e.g., VP2 and/or VP5 and/or VP7). This feature has important implications, e.g. to decrease the chance of non-responsiveness: vaccines designed to elicit immunity should preferably not be based on a single viral sequence or antigen but should include as many immunogenic sequences as feasible. VLPs based on alternative BTV serotypes can also be employed for successive immunizations: in order to evade anti-BTV responses elicited in a primary vaccination. This is an especially useful feature of the BTV system, not currently available in other antigen delivery systems (e.g., vaccinia, polio, Ty particles or Salmonella vectors).

The high levels production of CLPs and VLPs from baculovirus vectors suggest that this system may be adopted as a carrier system in which multiple foreign antigens can be presented to the immune systems to induce both cellular and humoral immunity.

In accordance with the invention, foreign antigens can be expressed as epitopes on protein components of CLPs and VLPs in a manner which enables the epitopes to be located in an internal site in the CLPs and VLPs. This can protect the foreign antigens from proteolysis and/or antibody attack until it reaches a desired location. This may for example be achieved with a chimeric VLP in which the VP7 is in chimeric form.

Similarly, having regard to the known interaction of VP3 with minor BTV proteins, formation of chimeric analogues of such minor proteins allows further opportunities of introducing foreign genes at sites which can lie in protected locations in the resulting chimeric VLPs.

REFERENCES

1. Valenzuela, P., Coit, D., Medina-Selby, A., Kuo, C. H., Van Nest, G., Burke, R. L., Bill, P., Urdea, M. S. and Graves, P. V. (1985). Bio/Technology 3:323–326.
2. Michel, M. L., Mancini, M., Riviere, Y., Dormont, D. and Tiollais, P. (1990). Journal of Virology 64:2452–2455.
3. Clarke, B. E., Newton, S. E., Carroll, A. R., Francis, M. J., Appleyard, G., Syred, A. D., Highfield, P. E., Rowlands, D. J. and Brown, F. (1987). Nature 330:381–384.
4. Evans, D. J., McKeating, J., Meredith, J. M., Burke, K. L., Katrak, K., John, A., Ferguson, M., Minor, P. D., Weiss, R. A., Almond, J. V. (1989). Nature 339:385–388.
5. Griffiths, J. C., Berrie, E. L., Holdworth, L. N., Moore, J. P., Harris, S. J., Senior, J. M., Kingsman, A. J., and Adams, S. E. (1991). J. Virol. 65:450–456.
6. French, T. J., Marshall, J. J. A. and Roy, P. (1990). J. Virol. 64:5695–5700.
7. Loudon, P. and Roy, P. (1991). Virology 180:798–802.
8. Ganem, D. and Varmus, H. E. (1987). H. E. Ann. Rev. Biochem. 56:651–633.
9. Galibert, F., Mandart, E., Fitoussi, R., Tiollais, P. and Charnay, P. (1979). Nature 281:646–650.
10. Maniatis, T., Fritsch, E. F. and Sambrook, J. (1982). "Molecular Cloning: A Laboratory Manual". Cold Spring Harbor Laboratory, Cold Spring Harbor, New York.
11. Matsuura, Y., Possee, R. D., Overton, H. A. and Bishop, D. H. L. (1987). J. Gen. Virol. 68:1233–1250.
12. Sanger, D. V., Nicklen, F. S. and Coulson, A. R. (1977). Proc. Natl. Acad. Sci. 74:5963–5467.
13. Kitts, P. A., Ayers, M. D. and Possee, R. D. (1990). Nucl. Acids Res. 18/19 pp. 5667.
14. Felgner, P. L., Gadek, T. R., Holm, M., Roman, R., Chan, H. W., Wenz, M., Northrop, J. P., Ringold, G. M. and Danielsen, M. (1987). Proceedings of Natl. Acad. of Sci. USA 84:7413–7417.
15. Oldfield, S., Adachi, A., Urakawa, T. Hirasawa, T. and Roy, P. (1990). J. Gen. Virol. 71:2649–2656.
16. Inamura, S., Ghiasi, H. and Roy, P. (1987). J. Gen Virol. 68:1627–1635.
17. French, T. J., Marshall, J. J. A. and Roy, P. (1990). J. Gen. Virol. 64:5695–5700
18. Smith, D. B., Johnson, K. S. (1988). Gene 67:31–40.
19. Prasad, B. V. V., Yamaguichi, S. and Roy, P. (1992). J. Virol. (in press).
20. Hewat, E. A., Booth, T. F., Wade, R. H. and Roy, P. (1991). J. Struct. Biol. (submitted).
21. Dehoux, P., Ribes, V., Sobczak, E. and Streeck, R. E. (1986). Gene 8:155–163.
22. Kniskern, P. J., Hagopian, A., Burke, P., Dunn, N., Emini, E. A., Miller, W. J., Yanasaki, S. and Ellis, R. W. (1988). Hepatology 8:82–87.

23. Itoh, Y., Hayakawa, Y. and Fujisawa, Y. (1986) Biocehm. Biophys. Res. Commun. 138:268–274.
24. Jacobs, E., Rutgers, T., Voet, P., Dewerchin, M., Cabezon, T. and De Wilde, M. (1989). Gene 80:279–291.
25. Possee, R. D. (1986). Virus Research. 5:43–59
26. Possee, R. D. and Howard, S. C. (1987). Nucleic Acids Research 15:10233–10248.
27. Maniatis, T., Fritsch, E. F. and Sambrook, J. (1982). Molecular Cloning: A Laboratory Manual. Cold Spring Harbor Laboratory Press, Cold Spring Harbor, N.Y.
28. Belyaev, A. S. et al, (1992) Virology 190:840–844.
29. French, T. J. and Roy, P. (1990) J. Virol. 64:1530–1536.
30. Crowe, J. S. et al (1991) Nucleic Acids Research 19:184.
31. Kitts P. A. and Possee R. D. (1993) Biotechniques (in press).
32. Matsuura et al (1987) J. General Virology 68:1627–1635.
33. Mobley, H. I. T. and Hausinger, R. P. (1989) Microbiol. Rev. 53:85–108
34. Wayler U. and Possee R. D. (1991) J. Gen. Virol.72:2967–2974.

I claim:

1. A particulate antigen in the form of a virus-like particle (VLP) or core-like particle (CLP) comprising bluetongue virus VP3 protein and a chimeric VP7 protein, wherein the chimeric VP7 protein comprises a foreign epitope fused to the N-terminus of bluetongue virus VP7.

2. The antigen of claim 1, further comprising native bluetongue virus VP7.

3. The antigen of claim 1, wherein the foreign epitope is from a rabies virus protein, a human hepatitis B virus protein, a human immunodeficiency virus protein, or a *Clostridium difficile* protein.

4. The antigen of claim 2, wherein the foreign epitope is from a bovine leukemia virus protein.

5. A particulate antigen in the form of a virus-like particle (VLP) or core-like particle (CLP) comprising bluetongue virus VP3 and VP7 proteins and a chimeric VP6 protein, wherein the chimeric VP6 protein comprises a foreign epitope fused to the C-terminus of bluetongue virus VP6.

6. The antigen of claim 5, wherein the foreign epitope is from a simian immunodeficiency virus protein.

7. An immunogenic composition comprising the particulate antigen of claim 1 or 5, in association with a therapeutically acceptable carrier or diluent.

8. A method of inducing an immunogenic response in a host, comprising the step of administering the composition of claim 7 to the host.

9. The method of claim 8, wherein the composition is administered to a mucosal surface of said host.

10. The method of claim 8, wherein the composition administered orally.

11. A method of inducing an immunogenic response in a host, comprising the step of administering the antigen of claim 1 or 5 to the host.

12. The method of claim 11, wherein the antigen is administered to a mucosal surface of said host.

13. The method of claim 11, wherein the antigen is administered orally.

14. A method of making a chimetic VLP or CLP, comprising assembling a VLP or CLP comprising bluetongue virus VP3 protein and a chimeric VP7 protein, wherein the chimeric VP7 protein comprises a foreign epitope fused to the N-terminus of bluetongue virus VP7.

15. The method of claim 14, further comprising assembling native bluetongue virus VP7 in the chimetic particle.

16. A method of making a chimeric VLP or CLP, comprising assembling a VLP or CLP comprising bluetongue virus VP3 and VP7 proteins and a chimeric VP6 protein, wherein the chimeric VP6 protein comprises a foreign epitope, fused to the C-terminus of bluetongue virus VP6.

17. The method of claim 14, 15, or 16, wherein the proteins are co-expressed in a recombinant cell.

18. The method of claim 17, wherein the cell is an insect cell.

* * * * *

SEQUENCE LISTING ( 1 ) GENERAL INFORMATION:

( i i i ) NUMBER OF SEQUENCES: 37

( 2 ) INFORMATION FOR SEQ ID NO:1:

( i ) SEQUENCE CHARACTERISTICS:
( A ) LENGTH: 37 base pairs
( B ) TYPE: nucleic acid
( C ) STRANDEDNESS: single
( D ) TOPOLOGY: unknown ( i i ) MOLECULE TYPE: DNA (genomic)

( x i ) SEQUENCE DESCRIPTION: SEQ ID NO:1:

GCGGGATCCC CTCAGACCCG GGGACACTAT CGCCGCA 37

( 2 ) INFORMATION FOR SEQ ID NO:2:

( i ) SEQUENCE CHARACTERISTICS:
( A ) LENGTH: 70 base pairs
( B ) TYPE: nucleic acid
( C ) STRANDEDNESS: single
( D ) TOPOLOGY: unknown ( i i ) MOLECULE TYPE: DNA (genomic)

( x i ) SEQUENCE DESCRIPTION: SEQ ID NO:2:

CTAGAAAATG AGCCAAGCCG ATCAAGGGTC CTTTTATGTC AATCATCAAA TTTTATTCCT 60

GCATCTCAAG 70

( 2 ) INFORMATION FOR SEQ ID NO:3:

( i ) SEQUENCE CHARACTERISTICS:
( A ) LENGTH: 66 base pairs
( B ) TYPE: nucleic acid
( C ) STRANDEDNESS: single
( D ) TOPOLOGY: unknown ( i i ) MOLECULE TYPE: DNA (genomic)

( x i ) SEQUENCE DESCRIPTION: SEQ ID NO:3:

CTTGAGATGC TGGAATAAAA TTTGATGATT GACATAAAAG GACCCTTGAT CGGCTTGGCT 60

CATTTT 66

( 2 ) INFORMATION FOR SEQ ID NO:4:

( i ) SEQUENCE CHARACTERISTICS:
( A ) LENGTH: 85 base pairs
( B ) TYPE: nucleic acid
( C ) STRANDEDNESS: single
( D ) TOPOLOGY: unknown -continued ( i i ) MOLECULE TYPE: DNA (genomic)

( x i ) SEQUENCE DESCRIPTION: SEQ ID NO:4:

CTAGAAAATG AGTTTAAATC AAACGGCACG GGCCTTCCCA GACTGTGCTA TATGTTGGGA 60

ACCTTCCCCT CCCTGGGCTC CCGAA 85

( 2 ) INFORMATION FOR SEQ ID NO:5:

( i ) SEQUENCE CHARACTERISTICS:
( A ) LENGTH: 81 base pairs
( B ) TYPE: nucleic acid
( C ) STRANDEDNESS: single
( D ) TOPOLOGY: unknown ( i i ) MOLECULE TYPE: DNA (genomic)

( x i ) SEQUENCE DESCRIPTION: SEQ ID NO:5:

TTCGGGAGCC CAGGGAGGGG AGGGTTCCCA ACATATAGCA CAGTCTGGGA AGGCCCGTGC 60

CGTTTGATTT AAACTCATTT T 81

( 2 ) INFORMATION FOR SEQ ID NO:6:

( i ) SEQUENCE CHARACTERISTICS:
( A ) LENGTH: 73 base pairs
( B ) TYPE: nucleic acid
( C ) STRANDEDNESS: single
( D ) TOPOLOGY: unknown ( i i ) MOLECULE TYPE: DNA (genomic)

( x i ) SEQUENCE DESCRIPTION: SEQ ID NO:6:

CTAGAAAATG AGTAAAATTC CTGATCCCCC TCAACCCGAC TTCCCTCAGC TGAACAGTGA 60

CTGGGTTCCC TCT 73

( 2 ) INFORMATION FOR SEQ ID NO:7:

( i ) SEQUENCE CHARACTERISTICS:
( A ) LENGTH: 69 base pairs
( B ) TYPE: nucleic acid
( C ) STRANDEDNESS: single
( D ) TOPOLOGY: unknown ( i i ) MOLECULE TYPE: DNA (genomic)

( x i ) SEQUENCE DESCRIPTION: SEQ ID NO:7:

AGAGGGAACC CAGTCACTGT TCAGCTGAGG GAAGTCGGGT TGAGGGGGAT CAGGAATTTT 60

ACTCATTTT 69

( 2 ) INFORMATION FOR SEQ ID NO:8:

( i ) SEQUENCE CHARACTERISTICS:
( A ) LENGTH: 28 base pairs
( B ) TYPE: nucleic acid
( C ) STRANDEDNESS: single
( D ) TOPOLOGY: unknown ( i i ) MOLECULE TYPE: DNA (genomic)

( x i ) SEQUENCE DESCRIPTION: SEQ ID NO:8:

GGCGAGATCT TAAGAGACGT TTAATGGG 28

( 2 ) INFORMATION FOR SEQ ID NO:9:

( i ) SEQUENCE CHARACTERISTICS:
( A ) LENGTH: 31 base pairs
( B ) TYPE: nucleic acid -continued ( C ) STRANDEDNESS: single
( D ) TOPOLOGY: unknown ( i i ) MOLECULE TYPE: DNA (genomic)

( i x ) FEATURE:
( A ) NAME/KEY: CDS
( B ) LOCATION: 13..30

( x i ) SEQUENCE DESCRIPTION: SEQ ID NO:9:

```
GGCAGATCTA CC ATG GAA ATT TTG GGG ATA G                    31
              Met Glu Ile Leu Gly Ile
               1               5
```

( 2 ) INFORMATION FOR SEQ ID NO:10:

( i ) SEQUENCE CHARACTERISTICS:
( A ) LENGTH: 6 amino acids
( B ) TYPE: amino acid
( D ) TOPOLOGY: linear ( i i ) MOLECULE TYPE: protein ( x i ) SEQUENCE DESCRIPTION: SEQ ID NO:10:

```
Met Glu Ile Leu Gly Ile
 1               5
```

( 2 ) INFORMATION FOR SEQ ID NO:11:

( i ) SEQUENCE CHARACTERISTICS:
( A ) LENGTH: 34 base pairs
( B ) TYPE: nucleic acid
( C ) STRANDEDNESS: single
( D ) TOPOLOGY: unknown ( i i ) MOLECULE TYPE: DNA (genomic)

( i x ) FEATURE:
( A ) NAME/KEY: CDS
( B ) LOCATION: 13..33

( x i ) SEQUENCE DESCRIPTION: SEQ ID NO:11:

```
GGCAGATCTA CC ATG GCA CAA AGA AAT GAG ATG T                34
              Met Ala Gln Arg Asn Glu Met
               1               5
```

( 2 ) INFORMATION FOR SEQ ID NO:12:

( i ) SEQUENCE CHARACTERISTICS:
( A ) LENGTH: 7 amino acids
( B ) TYPE: amino acid
( D ) TOPOLOGY: linear ( i i ) MOLECULE TYPE: protein ( x i ) SEQUENCE DESCRIPTION: SEQ ID NO:12:

```
Met Ala Gln Arg Asn Glu Met
 1               5
```

( 2 ) INFORMATION FOR SEQ ID NO:13:

( i ) SEQUENCE CHARACTERISTICS:
( A ) LENGTH: 29 base pairs
( B ) TYPE: nucleic acid
( C ) STRANDEDNESS: single
( D ) TOPOLOGY: unknown ( i i ) MOLECULE TYPE: DNA (genomic)

( x i ) SEQUENCE DESCRIPTION: SEQ ID NO:13:

```
CGCGAAGCTT CGCAAGCACT GTCAGAAGG                            29
```

( 2 ) INFORMATION FOR SEQ ID NO:14:

( i ) SEQUENCE CHARACTERISTICS:
( A ) LENGTH: 30 base pairs
( B ) TYPE: nucleic acid
( C ) STRANDEDNESS: single
( D ) TOPOLOGY: unknown ( i i ) MOLECULE TYPE: DNA (genomic)

( x i ) SEQUENCE DESCRIPTION: SEQ ID NO:14:

```
GCGCAAGCTT GGATCCTATT GATGGTCTCC                                      30
```

( 2 ) INFORMATION FOR SEQ ID NO:15:

( i ) SEQUENCE CHARACTERISTICS:
( A ) LENGTH: 176 base pairs
( B ) TYPE: nucleic acid
( C ) STRANDEDNESS: single
( D ) TOPOLOGY: unknown ( i i ) MOLECULE TYPE: DNA (genomic)

( i x ) FEATURE:
( A ) NAME/KEY: CDS
( B ) LOCATION: 15..176

( x i ) SEQUENCE DESCRIPTION: SEQ ID NO:15:

```
GGATCCTCTA GAAA ATG GAT CCG AAT TCC ACA ACC TTC CAC CAA ACT CTG      50
                Met Asp Pro Asn Ser Thr Thr Phe His Gln Thr Leu
                  1               5                  10

CAA GAT CCC AGA GTG AGA GGC CTG TAT TTC CCT GCT GGT GGC TCC AGT      98
Gln Asp Pro Arg Val Arg Gly Leu Tyr Phe Pro Ala Gly Gly Ser Ser
         15                  20                  25

TCA GGA ACA GTA AAC CCT GTT CCG ACT ACT GTC TCT CCC ATA TCG TCA     146
Ser Gly Thr Val Asn Pro Val Pro Thr Thr Val Ser Pro Ile Ser Ser
     30                  35                  40

ATC TTC TCG AGG ATT GGG GAT GGG GAC ACT                             176
Ile Phe Ser Arg Ile Gly Asp Gly Asp Thr
 45                  50
```

( 2 ) INFORMATION FOR SEQ ID NO:16:

( i ) SEQUENCE CHARACTERISTICS:
( A ) LENGTH: 54 amino acids
( B ) TYPE: amino acid
( D ) TOPOLOGY: linear ( i i ) MOLECULE TYPE: protein ( x i ) SEQUENCE DESCRIPTION: SEQ ID NO:16:

```
Met Asp Pro Asn Ser Thr Thr Phe His Gln Thr Leu Gln Asp Pro Arg
  1               5                  10                  15

Val Arg Gly Leu Tyr Phe Pro Ala Gly Gly Ser Ser Ser Gly Thr Val
             20                  25                  30

Asn Pro Val Pro Thr Thr Val Ser Pro Ile Ser Ser Ile Phe Ser Arg
         35                  40                  45

Ile Gly Asp Gly Asp Thr
     50
```

( 2 ) INFORMATION FOR SEQ ID NO:17:

( i ) SEQUENCE CHARACTERISTICS:
( A ) LENGTH: 94 base pairs
( B ) TYPE: nucleic acid
( C ) STRANDEDNESS: single ( D ) TOPOLOGY: unknown ( i i ) MOLECULE TYPE: DNA (genomic)

( i x ) FEATURE:
( A ) NAME/KEY: CDS
( B ) LOCATION: 8..49

( x i ) SEQUENCE DESCRIPTION: SEQ ID NO:17:

```
CTAGAAA ATG ACC ATC GAC GGC AAG AAG TAC TAC TTC AAC CCC GGG GAC    49
        Met Thr Ile Asp Gly Lys Lys Tyr Tyr Phe Asn Pro Gly Asp
         1               5                  10

TTTTACTGGT AGCTGCCGTT CTTCATGATG AAGTTGGGGC CCCTG                  94
```

( 2 ) INFORMATION FOR SEQ ID NO:18:

( i ) SEQUENCE CHARACTERISTICS:
( A ) LENGTH: 14 amino acids
( B ) TYPE: amino acid
( D ) TOPOLOGY: linear ( i i ) MOLECULE TYPE: protein ( x i ) SEQUENCE DESCRIPTION: SEQ ID NO:18:

```
Met Thr Ile Asp Gly Lys Lys Tyr Tyr Phe Asn Pro Gly Asp
 1               5                  10
```

( 2 ) INFORMATION FOR SEQ ID NO:19:

( i ) SEQUENCE CHARACTERISTICS:
( A ) LENGTH: 82 base pairs
( B ) TYPE: nucleic acid
( C ) STRANDEDNESS: single
( D ) TOPOLOGY: unknown ( i i ) MOLECULE TYPE: DNA (genomic)

( i x ) FEATURE:
( A ) NAME/KEY: CDS
( B ) LOCATION: 14..82

( x i ) SEQUENCE DESCRIPTION: SEQ ID NO:19:

```
GATCCTCTAG AAA ATG AGC CAA GCC GAT CAA TCC TTT TAT GTC AAT CAT    49
               Met Ser Gln Ala Asp Gln Ser Phe Tyr Val Asn His
                1               5                   10

CAA ATT TTA TTC CTG CAT CTC AAG GGG GAC ACT                        82
Gln Ile Leu Phe Leu His Leu Lys Gly Asp Thr
         15                  20
```

( 2 ) INFORMATION FOR SEQ ID NO:20:

( i ) SEQUENCE CHARACTERISTICS:
( A ) LENGTH: 23 amino acids
( B ) TYPE: amino acid
( D ) TOPOLOGY: linear ( i i ) MOLECULE TYPE: protein ( x i ) SEQUENCE DESCRIPTION: SEQ ID NO:20:

```
Met Ser Gln Ala Asp Gln Ser Phe Tyr Val Asn His Gln Ile Leu Phe
 1               5                  10                  15

Leu His Leu Lys Gly Asp Thr
             20
```

( 2 ) INFORMATION FOR SEQ ID NO:21:

( i ) SEQUENCE CHARACTERISTICS:
( A ) LENGTH: 100 base pairs
( B ) TYPE: nucleic acid -continued ( C ) STRANDEDNESS: single
( D ) TOPOLOGY: unknown ( i i ) MOLECULE TYPE: DNA (genomic)

( i x ) FEATURE:
( A ) NAME/KEY: CDS
( B ) LOCATION: 14..100

( x i ) SEQUENCE DESCRIPTION: SEQ ID NO:21:

```
GATCCACTAG AAA ATG AGT TTA AAT CAA ACG GCA CGG GCC TTC CCA GAC       49
               Met Ser Leu Asn Gln Thr Ala Arg Ala Phe Pro Asp
                 1               5                  10

TGT GCT ATA TGT TGG GAA CCT TCC CCT CCC TGG GCT CCC GAA GGG GAC      97
Cys Ala Ile Cys Trp Glu Pro Ser Pro Pro Trp Ala Pro Glu Gly Asp
        15                  20                  25

ACT                                                                 100
Thr
```

( 2 ) INFORMATION FOR SEQ ID NO:22:

( i ) SEQUENCE CHARACTERISTICS:
( A ) LENGTH: 29 amino acids
( B ) TYPE: amino acid
( D ) TOPOLOGY: linear ( i i ) MOLECULE TYPE: protein ( x i ) SEQUENCE DESCRIPTION: SEQ ID NO:22:

```
Met Ser Leu Asn Gln Thr Ala Arg Ala Phe Pro Asp Cys Ala Ile Cys
  1               5                  10                  15

Trp Glu Pro Ser Pro Pro Trp Ala Pro Glu Gly Asp Thr
            20                  25
```

( 2 ) INFORMATION FOR SEQ ID NO:23:

( i ) SEQUENCE CHARACTERISTICS:
( A ) LENGTH: 88 base pairs
( B ) TYPE: nucleic acid
( C ) STRANDEDNESS: single
( D ) TOPOLOGY: unknown ( i i ) MOLECULE TYPE: DNA (genomic)

( i x ) FEATURE:
( A ) NAME/KEY: CDS
( B ) LOCATION: 14..88

( x i ) SEQUENCE DESCRIPTION: SEQ ID NO:23:

```
GATCCACTAG AAA ATG AGT AAA ATT CCT GAT CCC CCT CAA CCC GAC TTC       49
               Met Ser Lys Ile Pro Asp Pro Pro Gln Pro Asp Phe
                 1               5                  10

CCT CAG CTG AAC AGT GAC TGG GTT CCC TCT GGG GAC ACT                  88
Pro Gln Leu Asn Ser Asp Trp Val Pro Ser Gly Asp Thr
        15                  20                  25
```

( 2 ) INFORMATION FOR SEQ ID NO:24:

( i ) SEQUENCE CHARACTERISTICS:
( A ) LENGTH: 25 amino acids
( B ) TYPE: amino acid
( D ) TOPOLOGY: linear ( i i ) MOLECULE TYPE: protein ( x i ) SEQUENCE DESCRIPTION: SEQ ID NO:24:

```
Met Ser Lys Ile Pro Asp Pro Pro Gln Pro Asp Phe Pro Gln Leu Asn
  1               5                  10                  15
```

-continued

Ser Asp Trp Val Pro Ser Gly Asp Thr
20 25

( 2 ) INFORMATION FOR SEQ ID NO:25:

( i ) SEQUENCE CHARACTERISTICS:
( A ) LENGTH: 24 base pairs
( B ) TYPE: nucleic acid
( C ) STRANDEDNESS: double
( D ) TOPOLOGY: unknown ( i i ) MOLECULE TYPE: DNA (genomic)

( i x ) FEATURE:
( A ) NAME/KEY: CDS
( B ) LOCATION: 1..24

( x i ) SEQUENCE DESCRIPTION: SEQ ID NO:25:

GCC AAT GTG GGG GAC CTT GTG ATG 24
Ala Asn Val Gly Asp Leu Val Met
1 5

( 2 ) INFORMATION FOR SEQ ID NO:26:

( i ) SEQUENCE CHARACTERISTICS:
( A ) LENGTH: 8 amino acids
( B ) TYPE: amino acid
( D ) TOPOLOGY: linear ( i i ) MOLECULE TYPE: protein ( x i ) SEQUENCE DESCRIPTION: SEQ ID NO:26:

Ala Asn Val Gly Asp Leu Val Met
1 5

( 2 ) INFORMATION FOR SEQ ID NO:27:

( i ) SEQUENCE CHARACTERISTICS:
( A ) LENGTH: 24 base pairs
( B ) TYPE: nucleic acid
( C ) STRANDEDNESS: double
( D ) TOPOLOGY: unknown ( i i ) MOLECULE TYPE: DNA (genomic)

( i x ) FEATURE:
( A ) NAME/KEY: CDS
( B ) LOCATION: 1..24

( x i ) SEQUENCE DESCRIPTION: SEQ ID NO:27:

CCA GGG AGG GAC CTC GGG AGG TGG 24
Pro Gly Arg Asp Leu Gly Arg Trp
1 5

( 2 ) INFORMATION FOR SEQ ID NO:28:

( i ) SEQUENCE CHARACTERISTICS:
( A ) LENGTH: 8 amino acids
( B ) TYPE: amino acid
( D ) TOPOLOGY: linear ( i i ) MOLECULE TYPE: protein ( x i ) SEQUENCE DESCRIPTION: SEQ ID NO:28:

Pro Gly Arg Asp Leu Gly Arg Trp
1 5

( 2 ) INFORMATION FOR SEQ ID NO:29:

( i ) SEQUENCE CHARACTERISTICS:
( A ) LENGTH: 15 base pairs

-continued ( B ) TYPE: nucleic acid
( C ) STRANDEDNESS: unknown
( D ) TOPOLOGY: unknown ( i i ) MOLECULE TYPE: DNA (genomic)

( i x ) FEATURE:
( A ) NAME/KEY: CDS
( B ) LOCATION: 1..15

( x i ) SEQUENCE DESCRIPTION: SEQ ID NO:29:

```
ATG GAT AAA ACT TTA                                    15
Met Asp Lys Thr Leu
 1               5
```

( 2 ) INFORMATION FOR SEQ ID NO:30:

( i ) SEQUENCE CHARACTERISTICS:
( A ) LENGTH: 5 amino acids
( B ) TYPE: amino acid
( D ) TOPOLOGY: linear ( i i ) MOLECULE TYPE: protein ( x i ) SEQUENCE DESCRIPTION: SEQ ID NO:30:

```
Met Asp Lys Thr Leu
 1               5
```

( 2 ) INFORMATION FOR SEQ ID NO:31:

( i ) SEQUENCE CHARACTERISTICS:
( A ) LENGTH: 15 base pairs
( B ) TYPE: nucleic acid
( C ) STRANDEDNESS: unknown
( D ) TOPOLOGY: unknown ( i i ) MOLECULE TYPE: DNA (genomic)

( i x ) FEATURE:
( A ) NAME/KEY: CDS
( B ) LOCATION: 1..12

( x i ) SEQUENCE DESCRIPTION: SEQ ID NO:31:

```
ATG GAT AGT ACT TTA                                    15
Met Asp Ser Thr
 1
```

( 2 ) INFORMATION FOR SEQ ID NO:32:

( i ) SEQUENCE CHARACTERISTICS:
( A ) LENGTH: 4 amino acids
( B ) TYPE: amino acid
( D ) TOPOLOGY: linear ( i i ) MOLECULE TYPE: protein ( x i ) SEQUENCE DESCRIPTION: SEQ ID NO:32:

```
Met Asp Ser Thr
 1
```

( 2 ) INFORMATION FOR SEQ ID NO:33:

( i ) SEQUENCE CHARACTERISTICS:
( A ) LENGTH: 15 base pairs
( B ) TYPE: nucleic acid
( C ) STRANDEDNESS: single
( D ) TOPOLOGY: unknown ( i i ) MOLECULE TYPE: DNA (genomic)

( i x ) FEATURE:
( A ) NAME/KEY: CDS

-continued ( B ) LOCATION: 1..15

( x i ) SEQUENCE DESCRIPTION: SEQ ID NO:33:

GCG AGA GGA GAT GTA 15
Ala Arg Gly Asp Val
1 5

( 2 ) INFORMATION FOR SEQ ID NO:34:

( i ) SEQUENCE CHARACTERISTICS:
( A ) LENGTH: 5 amino acids
( B ) TYPE: amino acid
( D ) TOPOLOGY: linear ( i i ) MOLECULE TYPE: protein ( x i ) SEQUENCE DESCRIPTION: SEQ ID NO:34:

Ala Arg Gly Asp Val
1 5

( 2 ) INFORMATION FOR SEQ ID NO:35:

( i ) SEQUENCE CHARACTERISTICS:
( A ) LENGTH: 15 base pairs
( B ) TYPE: nucleic acid
( C ) STRANDEDNESS: single
( D ) TOPOLOGY: unknown ( i i ) MOLECULE TYPE: DNA (genomic)

( i x ) FEATURE:
( A ) NAME/KEY: CDS
( B ) LOCATION: 1..15

( x i ) SEQUENCE DESCRIPTION: SEQ ID NO:35:

GCG AGA TCT GAT GTA 15
Ala Arg Ser Asp Val
1 5

( 2 ) INFORMATION FOR SEQ ID NO:36:

( i ) SEQUENCE CHARACTERISTICS:
( A ) LENGTH: 5 amino acids
( B ) TYPE: amino acid
( D ) TOPOLOGY: linear ( i i ) MOLECULE TYPE: protein ( x i ) SEQUENCE DESCRIPTION: SEQ ID NO:36:

Ala Arg Ser Asp Val
1 5

( 2 ) INFORMATION FOR SEQ ID NO:37:

( i ) SEQUENCE CHARACTERISTICS:
( A ) LENGTH: 10 amino acids
( B ) TYPE: amino acid
( C ) TOPOLOGY: linear ( i i ) MOLECULE TYPE: protein ( x i ) SEQUENCE DESCRIPTION: SEQ ID NO:37:

Thr Ile Asp Gly Lys Lys Tyr Tyr Phe Asn
1 5 10